US010154956B2

(12) United States Patent
Evilevitch

(10) Patent No.: US 10,154,956 B2
(45) Date of Patent: Dec. 18, 2018

(54) METHODS AND COMPOUNDS TO SUPPRESS VIRAL GENOME RELEASE AND PACKAGING

(71) Applicant: Carnegie Mellon University, Pittsburgh, PA (US)

(72) Inventor: Alex Evilevitch, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 15/222,379

(22) Filed: Jul. 28, 2016

(65) Prior Publication Data

US 2017/0027859 A1   Feb. 2, 2017

Related U.S. Application Data

(60) Provisional application No. 62/282,221, filed on Jul. 28, 2015.

(51) Int. Cl.
| | |
|---|---|
| *A61K 9/00* | (2006.01) |
| *A61K 33/24* | (2006.01) |
| *A61K 31/185* | (2006.01) |
| *A61K 31/194* | (2006.01) |
| *A61K 31/198* | (2006.01) |
| *A61K 31/08* | (2006.01) |
| *A61K 31/14* | (2006.01) |
| *C12N 7/00* | (2006.01) |
| *C12N 15/86* | (2006.01) |
| *C07H 21/00* | (2006.01) |
| *C08G 83/00* | (2006.01) |
| *C08G 81/00* | (2006.01) |
| *A61K 45/06* | (2006.01) |
| *A61K 38/06* | (2006.01) |
| *A61K 38/07* | (2006.01) |
| *A61K 31/16* | (2006.01) |
| *A61K 38/16* | (2006.01) |

(52) U.S. Cl.
CPC .......... *A61K 9/0014* (2013.01); *A61K 9/0043* (2013.01); *A61K 9/0046* (2013.01); *A61K 31/08* (2013.01); *A61K 31/14* (2013.01); *A61K 31/16* (2013.01); *A61K 31/185* (2013.01); *A61K 31/194* (2013.01); *A61K 31/198* (2013.01); *A61K 33/24* (2013.01); *A61K 38/06* (2013.01); *A61K 38/07* (2013.01); *A61K 38/16* (2013.01); *A61K 45/06* (2013.01); *C07H 21/00* (2013.01); *C08G 81/00* (2013.01); *C08G 83/003* (2013.01); *C12N 7/00* (2013.01); *C12N 15/86* (2013.01)

(58) Field of Classification Search
CPC ............ A61K 39/12; A61K 2039/5258; A61K 35/76; A61K 39/245; C12N 7/00; C12N 15/86; C07H 21/00; C08G 81/00; C08G 83/003
See application file for complete search history.

(56) References Cited

U.S. PATENT DOCUMENTS

| 6,190,650 B1* | 2/2001 | Matthews | A61K 31/785 |
| | | | 424/78.17 |
| 7,572,459 B2 | 8/2009 | Matthews et al. | |
| 2008/0286225 A1* | 11/2008 | Schonemyr | A01N 33/12 |
| | | | 424/78.32 |
| 2014/0127517 A1* | 5/2014 | Locklin | A01N 33/12 |
| | | | 428/426 |
| 2016/0213707 A1* | 7/2016 | Hedrick | A61K 31/785 |

OTHER PUBLICATIONS

Spoden GA, Besold K, Krauter S, Plachter B, Hanik N, Kilbinger AF, Lambert C, Florin L. Polyethylenimine is a strong inhibitor of human papillomavirus and cytomegalovirus infection. Antimicrob Agents Chemother. Jan. 2012;56(1):75-82. doi: 10.1128/AAC.05147-11. Epub Oct. 3, 2011.*
Cheng Y, Wang J, Rao T, He X, Xu T. Pharmaceutical applications of dendrimers: promising nanocarriers for drug delivery. Front Biosci. Jan. 1, 2008;13:1447-71. Review. PubMed PMID: 17981642.*
Cordova A, Deserno M, Gelbart WM, Ben-Shaul A. Osmotic shock and the strength of viral capsids. Biophys J. Jul. 2003;85(1):70-4.*
Khar RK, Jain GK, Warsi MH, Mallick N, Akhter S, Pathan SA, Ahmad FJ. Nano-vectors for the Ocular Delivery of Nucleic Acid based Therapeutics. Indian J Pharm Sci. Nov. 2010;72(6):675-88.*
Akers; "Parenteral Preparation"; Troy, DB, Editor, Remington: The Science and Practice of Pharmacy, 21st Ed.; Lippincott Williams & Wilkins; 2005; Chapter 41; pp. 802-849.
An et al. "Intermolecular forces between low generation PAMAM dendrimer condensed DNA helices: role of cation architecture"; Soft Matter; 2014; pp. 590-599; vol. 10:4.
Bauer et al. "Herpes Virus Genome, The Pressure is on"; Journal of the American Chemical Society; 2013; pp. A-F; vol. 135:30.
Chatterjee et al. "Studies on surfactant-biopolymer interaction. I. Microcalorimetric investigation on the interaction of cetyltrimethylammonium bromide (CTAB) and sodium dodecylsulfate (SDS) with gelatin (Gn), lysozyme (Lz) and deoxyribonucleic acid (DNA)"; Biophysical Chemistry; 2002; pp. 313-327; vol. 98.
Corbyn et al. "Re-dissolution and de-compaction of DNA-cationic surfactant complexes using non-ionic surfactants"; Physical Chemistry Chemical Physics; 2009; pp. 11568-11576; vol. 11.
Crowley; "Solutions, Emulsions, Suspensions, and Extract"; Troy, DB, Editor, Remington: The Science and Practice of Pharmacy, 21st Ed.; Lippincott Williams & Wilkins; 2005; Chapter 39; pp. 745-775.
Derouchey et al. "A comparison of DNA compaction by arginine and lysine peptides: A physical basis for arginine rich protamines"; Biochemistry; 2013; pp. 3000-3009; vol. 52:17.

(Continued)

*Primary Examiner* — Rachel B Gill
(74) *Attorney, Agent, or Firm* — The Webb Law Firm

(57) ABSTRACT

Provided herein are methods of suppressing viral nucleic acid, e.g. double-stranded (ds) DNA, genome release from or packaging of viruses having their nucleic acid genome packaged under stress in their capsid, and compositions useful for that purpose. The methods alter the ionic environment of the nucleic acid within the capsid and thereby prevent release of, and/or interfere with packaging of the viral genome.

8 Claims, 11 Drawing Sheets

Specification includes a Sequence Listing.

(56) References Cited

OTHER PUBLICATIONS

Derouchey et al. "Cation Charge Dependence of the Forces Driving DNA Assembly"; Biophysical Journal; 2010; pp. 2608-2615; vol. 99.
Derouchey et al. "Structural investigations of DNA-polycation complexes"; Eur. Phys. J.; 2005; pp. 17-28; vol. 16.
Evilevitch et al. "Effects of Salt Concentrations and Bending Energy on the Extent of Ejection of Phage Genomes"; Biophysical Journal; 2008; pp. 1110-1120; vol. 94.
Evilevitch et al. "Osmotic pressure inhibition of DNA ejection from phage"; Proceedings of the National Academy of the Sciences U.S.A.; 2003; pp. 9292-9295; vol. 100:16.
Gill et al. "Conserved retinoblastoma protein-binding motif in human cytomegalovirus UL97 kinase minimally impacts viral replication but affects susceptibility to maribavir"; Virology Journal; 2009; pp. 1-5; vol. 6:9.
Guillot et al. "Polyelectrolyte-surfactant complexes at interfaces and in bulk"; Journal of Physics: Condensed Matter; 2003; pp. S219-S224; vol. 15.
Hagman; "Sterilization"; Troy, DB, Editor, Remington: The Science and Practice of Pharmacy, 21st Ed.; Lippincott WIlliams & Wilkins; 2005; Chapter 41; pp. 776-801.
Ivanovska et al. "Internal DNA pressure modifies stability of WT phage"; Proceedings of the National Academy of the Sciences U.S.A.; 2007; pp. 9603-9608; vol. 104:23.
Jeembaeva et al. "DNA Heats Up: Energetics of Genome Ejection from Phage Revealed by Isothermal Titration Calorimetry"; J. Mol. Biol.; 2009; pp. 1-9; vol. 395.
Lander et al. "DNA bending-induced phase transition of encapsidated genome in phage λ"; Nucleic Acids Research; 2013; pp. 4518-4524; vol. 41:8.
Li et al. "Ionic switch controls the DNA state in phage λ"; Nucleic Acids Research; 2015; pp. 1-11.
Liu et al. "Solid-to-fluid-like DNA transition in viruses facilitates infection"; Proceedings of the National Academy of the Sciences U.S.A.; 2014; pp. 1-6; vol. 111:41.
McCarthy, "The Effects of Magnesium Starvation on the Ribosome Content of *Escherichia coli*"; Biochimica et Biophysica Acta; 1962; pp. 880-888; vol. 55.

Morel et al., "Enhanced nitrate ultrafiltration by cationic surfactant"; Journal of Membrane Science; 1991; pp. 1-12; vol. 56.
Ojala et al., "Herpes Simplex Virus Type 1 Entry into Host Cells: Reconstitution of Capsid Binding and Uncoating at the Nuclear Pore Complex In Vitro"; Molecular and Cellular Biology; 2000; pp. 4922-4931; vol. 20:13.
Prichard et al., "A rapid DNA hybridization assay for the evaluation of antiviral compounds against Epstein-Barr virus"; J Virol Methods; 2007; pp. 86-90; vol. 144:1-2.
Prichard et al., "Activity and Mechanism of Action of N-Methanocarbathymidine against Herpesvirus and Orthopoxvirus Infections"; Antimicrobial Agents and Chemotherapy; 2006; pp. 1336-1341; vol. 50:4.
Prichard et al., "Benzimidazole Analogs Inhibit Human Herpesvirus 6"; Antimicrobial Agents and Chemotherapy; 2011; pp. 2442-2445; vol. 55:5.
Prichard et al., "Inhibition of Herpesvirus Replication by 5-Substituted 4'-Thiopyrimidine Nucleosides"; Antimicrobial Agents and Chemotherapy; 2009; pp. 5251-5258; vol. 53:12.
Prichard et al., "Synthesis and Antiviral Activities of Methylenecyclopropane Analogs with 6-Alkoxy and 6-Alkylthio Substitutions That Exhibit Broad-Spectrum Antiviral Activity against Human Herpesviruses"; Antimicrobial Agents and chemotherapy; pp. 3518-3527; vol. 57:8.
Rau et al., "Direct measurement of temperature-dependent solvation forces between DNA double helices"; Biophysical Journal; 1992; pp. 260-271; vol. 61.
Rau et al., "Direct measurement of the intermolecular forces between counterion-condensed DNA double helices: Evidence for long range attractive hydration forces"; Biophysical Journal; 1992; pp. 246-259; vol. 61.
Sae-Ueng et al., "Solid-to-fluid DNA transition inside HSV-1 capsid close to the temperature of infection"; Nature Chemical Biology; 2014; pp. 861-867; vol. 10.
Todd et al., "Attractive Forces between Cation Condensed DNA Double Helices"; Biophysical Journal; 2008; pp. 4775-4782; vol. 94.
Yang et al., "Incomplete Ion Dissociation Underlies the weakened Attraction between DNA Helices at High Spermidine Concentrations"; Biophysical Journal; 2005; pp. 1932-1940; vol. 89.
Bourne et al. "Dendrimers, a new class of candidate topical microbicides with activity against herpes simplex virus infection"; Antimicrobial Agents and Chemotherapy; 2000; pp. 2471-2474; vol. 44, No. 9.

\* cited by examiner

G0 PAMAM dendrimer:

G1 PAMAM dendrimer:

| marker | osmolyte concentration (w/w %) | | Part a: viral DNA from unbound capsids | Part b: free viral DNA in the extra-nuclear fluid | Part c: non-ejected viral DNA | Part d: ejected viral DNA in the nucleoplasm | Control*: DNA detected after treating with Dnase I | Total copy number: (a+b+c+d) |
|---|---|---|---|---|---|---|---|---|
| | Dextran - 155k | PEG - 8k | Copy number (×10$^7$) | | | | | |
| ICP0 | 0 | 0 | 0.506 ± 0.176 | 15.093 ± 0.866 | 4.371 ± 0.332 | 186.543 ± 99.970 | | 206.51 ± 99.97 |
| | 30 | 0 | 1.903 ± 0.115 | 1.157 ± 0.097 | 3.447 ± 0.126 | 2.360 ± 0.231 | 0.922 ± 0.068 | 8.87 ± 0.30 |
| | 0 | 30 | 0.022 ± 0.001 | 0.005 ± 0.000 | 560.646 ± 218.366 | 0.883 ± 0.043 | | 561.56 ± 218.37 |
| VP16 | 0 | 0 | 5.982 ± 0.698 | 57.966 ± 1.800 | 42.577 ± 8.205 | 4527.282 ± 3336.223 | | 4633.8 ± 3335.8 |
| | 30 | 0 | 37.684 ± 1.123 | 13.303 ± 2.998 | 63.063 ± 10.621 | 21.532 ± 6.196 | 8.584 ± 0.816 | 135.58 ± 12.706 |
| | 0 | 30 | 0.124 ± 0.008 | 0.187 ± 0.136 | 5434.512 ± 4161.112 | 12.336 ± 2.068 | | 5447.2 ± 4161.1 |

*Fig. 5*

METHODS AND COMPOUNDS TO SUPPRESS VIRAL GENOME RELEASE AND PACKAGING

CROSS REFERENCE TO RELATED APPLICATIONS

This application claims the benefit of U.S. Provisional Patent Application No. 62/282,221, filed Jul. 28, 2015, which is incorporated herein by reference in its entirety.

STATEMENT REGARDING FEDERAL FUNDING

This invention was made with government support under Grant Nos. CHE-1152770 and CHE-1507694, awarded by the National Science Foundation. The government has certain rights in this invention.

BACKGROUND

Provided herein are method of suppressing viral genome release and related compositions.

Viruses are among the simplest biological organisms. They typically consist of a viral genome within a protein capsid, whose function is to protect the genome and to provide a specific strategy for the early steps of infection. Despite their simplicity, viruses exhibit extreme diversity and are highly prone to mutations. This limits the efficiency of current antiviral therapies, which are often focused on the specificity of viral replication. The past decade has seen the emergence of a new interdisciplinary approach, called "Physical Virology", providing tremendous opportunities for the elucidation of the general physical mechanisms involved in virus development and infection.

Compositions and methods useful in treatment or prevention of viral infection that are resistant to viral mutation are therefore desirable.

SUMMARY

Provided herein are methods of suppressing viral nucleic acid, e.g. double-stranded (ds) DNA, genome release from viral capsid or packaging of viruses having their nucleic acid genome packaged under stress in their capsid, and compositions useful for that purpose. The methods alter the ionic environment of the nucleic acid within the capsid and thereby prevent release of, and/or interfere with packaging of the viral genome.

According to one aspect, provided is a method of treating an infection in a patient of a virus having a stressed nucleic acid genome in a capsid, comprising contacting a virus particle of the virus with an amount of a composition comprising a polycationic polypeptide, a polycationic polymer, a DNA condensing protein, a cationic dendrimer, a branched polyamine, an inorganic cationic metal complex, a cationic surfactant, an osmolyte, and/or a chelating agent in an amount effective to inhibit release of the nucleic acid from the capsid of the virus particle and/or to interfere with packaging of viral genomes, thereby treating the virus infection.

BRIEF DESCRIPTION OF THE DRAWINGS

(FIG. 3A) Enthalpy of DNA ejection per virion (J) from WT DNA phage versus temperature, $\Delta H_{ej}$, in $MgCl_2$ Tris-buffers with varying $MgCl_2$ concentrations. Dashed lines are drawn to guide the eye. The vertical dashed lines indicate the DNA transition point. Vertical error bars are SEs. (FIG. 3B) DNA diffraction peak area as a function of temperature for WT DNA phage λ in $MgCl_2$ Tris-buffers with varying $MgCl_2$ concentrations. A constant has been added to each set of area values corresponding to one Mg-concentration in order to vertically separate the data for visual comparison. The vertical dashed lines indicate the DNA transition point. The vertical error bars are from the non-linear fitting. (FIG. 3C) Comparison between DNA transition temperatures determined by ITC and SAXS as a function of $MgCl_2$ concentration in Tris-buffer.

(FIG. 4A) DNA diffraction peak area as a function of temperature for WT DNA phage λ in 10 mM $MgCl_2$ Tris-buffer without and with 1 mM spermine (4+). (FIG. 4B) DNA diffraction peak area as a function of temperature for 78% of WT DNA length phage λ in 10 mM $MgCl_2$-Tris buffer without and with 20 mM EDTA. (FIG. 4C) DNA-DNA interaxial spacing d as a function of temperature for 78% of WT DNA length phage λ in 10 mM $MgCl_2$ Tris-buffer without and with 20 mM EDTA. In A, B and C, the vertical error bars are from the non-linear fitting of the DNA diffraction peak with a Gaussian function with linear background subtraction. The dashed line is drawn to guide the eye.

FIG. 5 is a table showing Quantification of HSV-1 DNA copy number in the in vitro genome translocation system by qPCR.

Error bar in (B) and (D) are standard derivations in copy numbers from three PCR reactions repeated in identical conditions. Error bar in (C) and (E) are propagated standard deviations derived using $\sigma(\Sigma a,b,c,d)=\sqrt{\sigma_a^2+\sigma_b^2+\sigma_c^2+\sigma_d^2}$. *Explanation of figure captions: control=no osmolytes.

Figure 11:
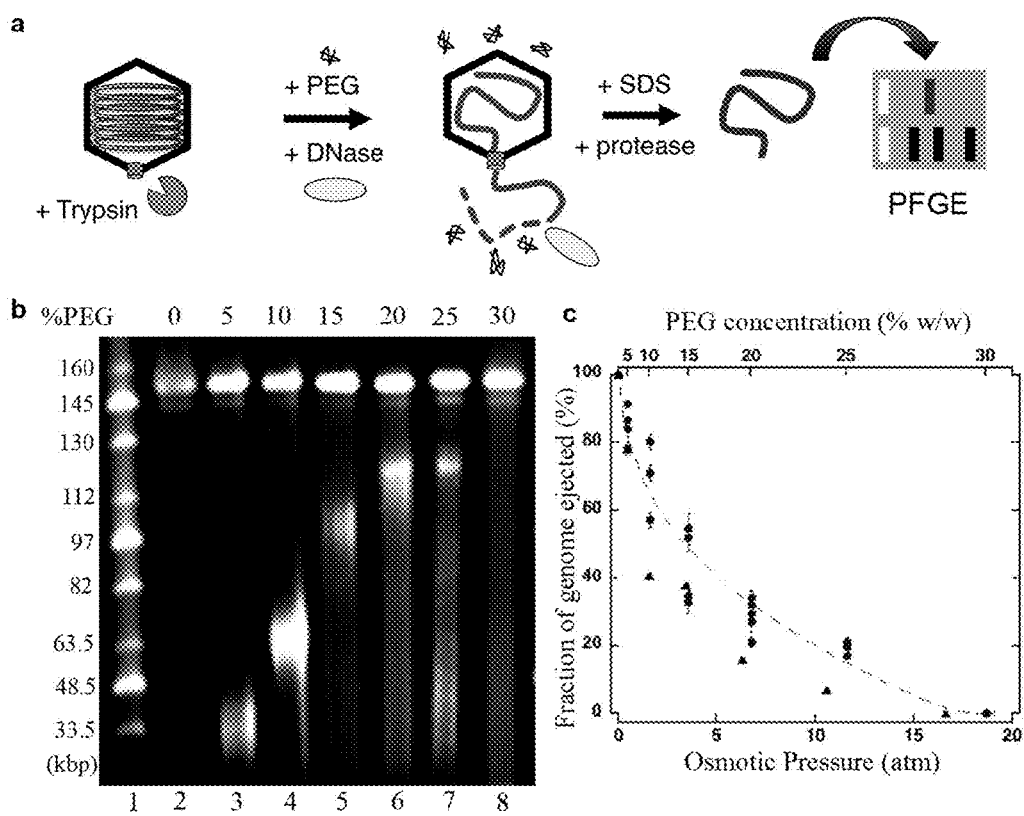

FIG. 11: Osmotic pressure suppression of DNA ejection from HSV-1 in a nuclear-free system. (A) Schematic of experimental assay. DNA ejection from HSV-1 capsids is initiated by trypsin digestion in the presence (or absence) of PEG and DNase I at 37° C. Non-ejected DNA was extracted from capsids by sodium dodecyl sulfate (SDS) and protease K treatment and analyzed by pulse field gel electrophoresis (PFGE). (B) PFGE of osmotically suppressed DNA remaining inside viral capsids in the presence of varying concentrations of PEG (lanes 2-8). (C) Fraction of viral genome ejected from HSV-1 capsids (circles) as a function of the external osmotic pressure. Error bars represent the standard deviation of the gel band intensity profile. The dashed line is shown as a visual guide for the fraction ejected from HSV-1.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. As used herein "a" and "an" refer to one or more.

As used herein, the term "patient" or "subject" refers to members of the animal kingdom including but not limited to human beings and "mammal" refers to all mammals, including, but not limited to human beings.

As used herein, the "treatment" or "treating" of a wound or defect means administration to a patient by any suitable dosage regimen, procedure and/or administration route of a composition, device or structure with the object of achieving a desirable clinical/medical end-point, including attracting progenitor cells, healing a wound, correcting a defect, etc.

As used herein, the terms "comprising," "comprise" or "comprised," and variations thereof, are open ended and do not exclude the presence of other elements not identified. In contrast, the term "consisting of" and variations thereof is intended to be closed, and excludes additional elements in anything but trace amounts.

As used herein, a "polymer" is a compound formed by the covalent joining of smaller molecules, which are referred to herein as monomers before incorporation into the polymer and residues, or polymer subunits, after incorporated into a polymer. A "copolymer" is a polymer comprising two or more different residues. Non-limiting examples of monomers, in the context of the copolymers described herein, include:

In many double-stranded DNA viruses (dsDNA viruses), the genome is often hundreds of times longer than the dimensions of the capsid into which it is packaged, and this results in high internal pressure due to the repulsive negative charges on the densely packaged DNA. Indeed, high mechanical pressure in double-stranded DNA bacterial viruses (phages) has recently been demonstrated. During infection, the phage binds to the receptor on the bacterial cell surface and the pressure injects the genome into the cell, at least in part, while the empty capsid remains outside the cell. This initiates a series of events, eventually leading to hundreds of viral genomes, preassembled capsids, and viral tails that are the direct precursors to the assembled, infectious virus. During phage assembly, a motor complex (the terminase enzyme) specifically recognizes viral DNA and then binds to the portal complex situated at a unique vertex of the icosahedral capsid; the portal is a ring-like structure that provides a hole through which DNA enters the capsid during assembly and exits during infection. The terminase motors, which utilize ATP hydrolysis to drive DNA into the capsid, are among the most powerful biological motors characterized to date. For instance, the bacteriophage λ terminase motor packages DNA to near-crystalline density, which generates an internal pressure in excess of 30 atm. Commensurate with this requirement, the λ terminase motor exerts forces greater than 50 pN during the terminal stages of genome packaging. Similar features are observed in many bacteriophages and the eukaryotic herpes virus groups. In the latter case, genome packaging occurs in the nucleus of an infected cell, following a pathway that is remarkably similar to that of the phage system; that is, a terminase motor specifically packages viral DNA into the interior of a pre-assembled procapsid through a unique portal vertex.

Further, although DNA is always condensed inside the cell, it is not condensed to the same extent as inside a viral capsid. Other than in sperm nuclei, in vivo packaging densities range from ~5-10% by volume. DNA confined in viral capsids, on the other hand, is at the extreme end of the packaging scale, where it is confined up to 55% by volume, forming a hexagonally-ordered structure. At only a few angstroms of DNA-DNA surface separation (e.g., 7 Å surface separation in the wild-type (WT) DNA length of 48,500 bp packaged in phage λ), hexagonally ordered DNA has been shown to have very restricted mobility.

Within the capsid, dsDNA packaged in both HSV-1 and phage λ is two orders of magnitude longer than the diameter of the capsid. This tight genome confinement leads to strong DNA-DNA repulsions and bending stress on the genome generating pressure of tens of atmospheres on the capsid walls. The encapsidated DNA is at the extreme end of the packing limit (reaching packing fraction of 55% by volume), with only ~7-12 Å of interhelical surface separation. DNA at this packing density assumes a hexagonally ordered structure with very restricted mobility (see e.g., Bauer D., et al., "Herpes Virus Genome, The Pressure is On", Journal of the American Chemical Society, Jul. 5, 2013, 135 (30), pp 11216-11221, incorporated herein by reference in its entirety).

The concept of virion metastability implies that the virus, in order to successfully replicate, must be sufficiently stable to prevent spontaneous release of its genome outside the cell between infection events, and at the same time be unstable enough to release its genome during infection. Viral particles are therefore not inert structures and have not attained the minimum free energy conformation, separated by an energetic or kinetic barrier, prior to cell attachment and entry. Thus, viral structure plays an active role in genome delivery to the host cell. Viral metastability is mostly associated with structural transformations in the nucleocapsid and/or surrounding lipid envelop in response to changes in the virion's environment. However, this does not apply to motor-packaged double-stranded (ds) DNA viruses (e.g. dsDNA phages and eukaryotic dsDNA viruses such as Herpesviruses), or to other viruses, such as some lentiviruses (e.g. HIV), whose capsid remains intact after the genome is released into a cell through a portal opening in the capsid structure. (See, generally, T. Liu, et al., "Solid-to-Fluid DNA Transition in Viruses Facilitates Infection". PNAS 2014 111 (41) 14675-14680, incorporated herein by reference in its entirety).

Ejection of genomic material from pressurized viral capsids requires sufficient mobility of the genomic material within the capsid, For example, Coulomb electrostatic sliding friction between neighboring DNA helices is thought to play a significant role in DNA mobility at high packing densities in the viral capsids. Interhelical sliding friction leads to a kinetically-trapped, glassy DNA state inside the capsid. This high-friction genome state significantly affects the rates of DNA packaging in vitro. This occurs from dragging closely-packed, negatively charged DNA helices past other helices. Despite decades of investigations of the encapsidated genome structure and its energetics, it is not known what provides the required mobility to the hexagonally ordered viral DNA during the initiation of its ultrafast ejection, reaching 60,000 bp/s.

It has been found that it is the encapsidated DNA, rather than the capsid itself in these viruses that is metastable. Specifically, double-stranded DNA (dsDNA) packaged in phage λ and human Herpes Simplex virus 1 (HSV-1) undergoes a solid-to-fluid-like structural transition facilitating initiation of viral genome ejection as well as its initial translocation from the capsid during infection.

For phage λ, DNA layers closest to the capsid's center undergo a disordering transition induced by an increase in temperature. This occurs from an increase in interstrand repulsions, due to DNA packing defects, leading to stronger genome stress (as described in detail below). DNA disordering at the transition temperature leads to a locally lower packing density in the center of the capsid, maximizing DNA-DNA spacings which in turn reduces interstrand repulsions. This leads to a more mobile, or fluid, DNA state which can be readily ejected from the capsid. Thus, below the transition temperature, viral DNA is trapped in a solid-like metastable state inside the capsid, which delays the initiation of its spontaneous release from the capsid and deactivation of the virion. An increase in temperature induces the necessary mobility of the packaged genome, facilitating its release and infection of the bacterial cell. Indeed, using single molecule fluorescence measurements and a plaque assay, the inventors confirmed a marked increase in the rate of infection spread at temperatures above that of DNA transition. However, it is important to emphasize that they also found that the transition temperature is directly coupled to the critical DNA stress value in the capsid. The encapsidated genome stress is, in turn, regulated by DNA counterions and packaged DNA density, both affecting the repulsive interactions between DNA helices. It was shown that removal of polyvalent cations from the encapsidated DNA environment through addition of chelating agents, also prevents solid-to-fluid-like DNA transition in the capsid, with packaged DNA remaining in a solid-like state. This in turn prevents DNA release from the capsid and inhibits infection. Therefore, chelating agents can be used as a drug interfering with viral infection.

The packaged genome density in phage λ presents the most energetically and structurally optimized balance between genome mobility and its internal stress, both of which are required for efficient DNA ejection from the capsid. It is shown that DNA transition occurs once the critical DNA stress level in the capsid is reached. The genome stress is generated by interstrand repulsive interactions, packing defects and DNA bending stress, which are in turn controlled by the temperature and the ionic conditions of the surrounding solution. For example, it is shown that at the most favorable external $Mg^{2+}$ concentration for phage λ adsorption to E. coli and subsequent replication (~10-20 mM $Mg^{2+}$), the DNA transition in the capsid occurs precisely at the physiologic temperature of infection (37° C.). This suggests a remarkable evolutionary adaptation of the DNA transition mechanism in phage λ to the temperature and ionic environment of its host. Thus, DNA transition in the capsid is physiologically relevant, which suggests its importance for viral replication. These observations are translatable to packaging and ejection of nucleic acids in eukaryotic viruses, such as species of the order Herpesvirales (herpesviruses, such as Herpes simplex virus 1 (HSV-1), Herpes simplex virus 2 (HSV-2), Human cytomegalovirus (CMV), Varicella Zoster virus (VZV), Epstein Barr virus (EBV), Human herpes virus 6 (HHV-6), Human herpes virus 7 (HHV-7), Human herpes virus 8 (HHV-8)) all of which have human or veterinary relevance.

Other eukaryotic DNA viruses have stressed nucleic acids, and are therefore susceptible to treatments that affect the ionic environment within the capsid and prevent release of the genome and/or packaging of the genome. These viruses include eukaryotic reoviruses (dsRNA), e.g. gastrointestinal rotavirus. During genome packaging eukaryotic reoviruses replicate single-stranded RNA to double-stranded RNA inside the capsid analogous to dsRNA bacteriophage fi6, which results in genome packaging densities similar to dsDNA viruses (such as Herpesviruses). Such intracapsid replication could be regulated, at least in part, by the generation of an internal pressure resulting from the increasing genome packaging density as newly synthesized dsRNA continues to fill the internal capsid volume. Furthermore, as packaged single-stranded RNA is replicated into double-stranded RNA within the capsid, pressure-induced genome ordering may help organize the tightly packaged genome in a manner that facilitates efficient intracapsid transcription. The methods described herein can interfere with this pressure regulated genome transcription.

Another group of viruses where the methods described herein can work are ssRNA retroviruses (e.g. lentiviruses, such as HIV). ssRNA HIV virus reverse-transcribes ssRNA to dsDNA inside the capsid. After that, the HIV capsid docks to the cell nucleus (similar to Herpesviruses) and releases its dsDNA into the cell nucleus (these steps of infection have been very recently demonstrated). It is therefore highly likely that the reversely transcribed dsDNA inside HIV capsid can be pressurized. The methods described herein therefore are expected to be able to interfere with either reverse transcription process from ssRNA to dsDNA inside the HIV capsid, or with dsDNA release from HIV capsid into nucleus.

Adenoviruses (a dsDNA virus) have also been proposed to have stressed dsDNA inside the capsid which is subsequently released into cell nucleus. Thus, once again, the methods described herein could inhibit the release of pressurized dsDNA from Adenovirus.

Therefore, provided herein are methods of suppressing viral genome release, as well as methods of treating viral infections caused by herpesviruses, such as Herpes simplex virus 1 (HSV-1), Herpes simplex virus 2 (HSV-2), Human cytomegalovirus (CMV), Varicella Zoster virus (VZV), Epstein Barr virus (EBV), Human herpes virus 6 (HHV-6), Human herpes virus 7 (HHV-7), Human herpes virus 8 (HHV-8), lentiviruses, such as HIV, reoviruses, and adenoviruses.

Also provided herein are compositions useful for suppressing viral genome release or replication, as well as methods of treating viral infections.

As used herein, a "virus containing a stressed genome," a virus containing a stressed nucleic acid (or RNA or DNA), or a virus capsid containing a stressed genome, nucleic acid, RNA, or DNA refers to a virus capsid in which the pressure of the genome in the capsid is greater than 1 atmosphere, caused for example by the stresses of bending of the nucleic acid genome and/or interstrand repulsion.

Methods and compositions described herein perturb the ionic environment of a virus having a stressed genome in its capsid, thereby condensing or expanding the genome and decreasing internal capsid pressure, thereby preventing or otherwise inhibiting viral release and/or packaging. Therefore, compounds, such as a polycationic polypeptide, a polycationic polymer, a DNA condensing protein, a cationic dendrimer, a branched polyamine, an inorganic cationic metal complex, a cationic surfactant, an osmolyte, and/or a chelating agent, are administered in effective amounts to treat a disease or condition caused by the virus.

Pressurized DNA as a New Drug Target:

In one aspect, herpesviruses are a leading cause of human viral disease, while development of drug resistance to the current therapies is a serious problem in immunocompromised patients where they are most needed. Described herein are mechanisms for perturbing infectivity and replication of herpesviruses and therefore treating conditions caused by the virus. The findings are of fundamental importance for herpes virology. Provided herein are mutation-resistant compositions and methods of treating herpes infections. Specifically, compositions useful to perturb the internal DNA pressure in herpes capsids as new classes of mutation-resistant antiviral treatments to interfere with viral replication.

The methods and compositions described herein interfere with the physical mechanism of genome packaging or ejection during viral replication by changing the ionic environment of a stressed nucleic acid, such as a DNA within a viral capsid. These drug molecules are small enough to permeate the viral capsid, for example 4 kDa or less, and bind to DNA through electrostatic interaction. The DNA pressure in the capsid is generated by DNA-DNA repulsive interactions between negatively charged DNA strands and DNA bending energy (double-stranded DNA is a stiff polymer). The highly positively charged drug molecules permeate the capsid and bind to highly negatively charged DNA strands in the capsid. This binding strongly reduces the DNA-DNA repulsive interactions and also DNA bending energy (both responsible for intracapsid DNA pressure). This intracapsid DNA condensation by the cationic multivalent drug molecules prevents DNA release from the capsid by reducing the internal capsid pressure and making the virus non-infectious. Binding affinity of these positively charged drug molecules is strongly dependent on the packing density of the DNA. Although DNA is always condensed inside the cell, it is not condensed to the same extent as inside a Herpes capsid. In vivo packaging densities range from 5-10% by volume. DNA confined in viral capsids, on the other hand, is at the extreme end of the packaging scale, where it is confined to 40-60% by volume. This leads to robust preferential binding mechanism to tightly condensed herpes DNA as opposed to cellular genomic DNA. The drug molecules below have strongest affinity for high-density negative charges on DNA in condensed dsDNA phases inside the capsid. Densely packaged Herpes DNA (in all known Herpes viruses) has a significantly higher density of negative charges than cellular genomic DNA which leads to preferential binding of those polyvalent cationic drug molecules to packaged viral genomes. This selectivity for polyvalent cationic drug binding reduces the possibility for off-target binding to non-viral DNA inside the cell.

Figure 1A:
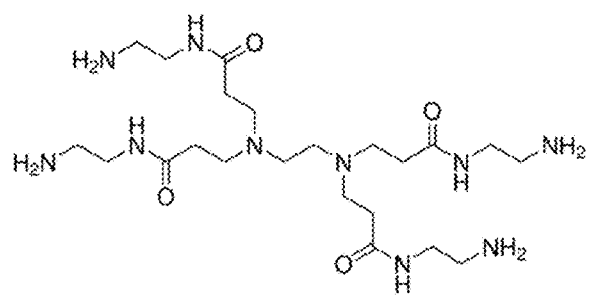
FIGS. 1A and 1B depict exemplary ethylenediamine core generation 0 (G0, FIG. 1A) and generation 1 (G1, FIG. 1B) dendrimers.
Figure 1B:
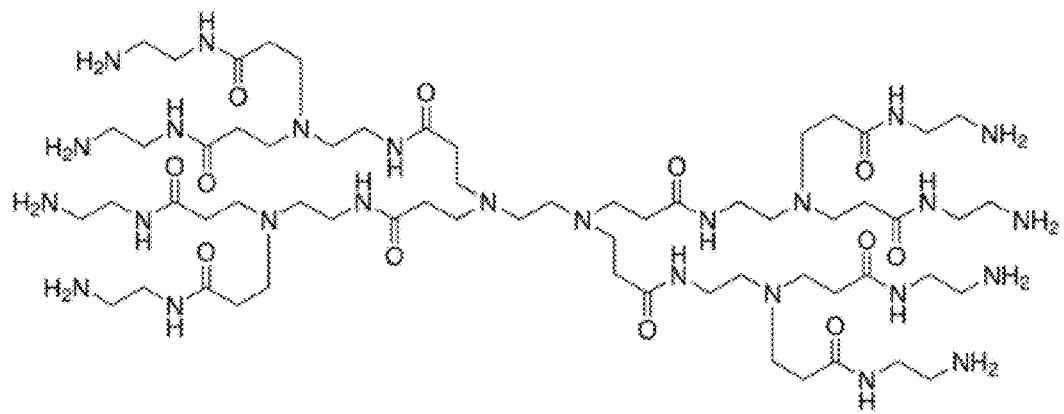

Small polyvalent cationic molecules, e.g., able to permeate the pores in the protein capsid in order to condense the encapsidated DNA and osmolytes (which must be large enough to not permeate the capsid and therefore generate an external osmotic pressure which suppresses DNA ejection from the virus, as we have shown), will efficiently condense the nucleic acid, e.g. DNA, in virus capsids containing a stressed genome, such as dsDNA virus capsids, such as eukaryotic dsDNA virus capsids, for example a herpesvirus capsid, and significantly reduce the internal pressure, making the virus non-infectious. Useful polycations (polyvalent cationic compositions having 2 or more positive charges (+2)) include, but not limited to: salmon protamine; $Co(NH_3)_6^{3+}$, $Mn^{2+}$; a biogenic amine, such as dimethylamine $((CH_2)_3NH)$ hydrochloride, putrescine $(NH_2(CH_2)_4NH_2)$ dihydrochloride, spermidine $(H_2N(CH_2)_3NH(CH_2)_4NH_2)^{3+}$, spermine $(H_2N(CH_2)_3NH(CH_2)_4—NH(CH_2)_3NH_2)^{4+}$; arginine polypeptides (e.g. ranging in charge from +2 to +8, poly-L-arginine hydrochloride) and lysine polypeptides [e.g. dilysine dihydrochloride (di-lys$^{2+}$), trilysine (tri-lys$^{3+}$), tetralysine (tetra-lys$^{4+}$), pentalysine (penta-lys$^{5+}$), poly-L-lysine hydrochloride], L-ornithine hydrochloride (e.g. Orn$^{3+}$ and Orn$^{4+}$), poly-L-histidine, mixed lysine-arginine peptides (e.g. Lys$_3$-Arg$_3^{6+}$, (Lys-Arg)$_3^{6+}$), branched polyethylenimine (e.g. bPEI MW 600). Also, cationic dendrimers, such as poly(amidoamine) (PAMAM) dendrimers (e.g., from Dendritech, such as low generation PAMAM dendrimers, e.g., G0-PAMAM (+4) and G1-PAMAM (+8)) (FIGS. 1A and 1B, respectively). Hyperbranched PAMAM molecules are compared to those of linear arginine peptides of the same net charge (tetra-arginine [$R4^{4+}$] and octa-arginine [$R8^{8+}$]). Also, DNA condensing proteins, such as histone proteins (e.g. linker: H1; core: H2A, H2B, H3, H4), and transition nuclear proteins (TP1 and TP2). Also, cationic surfactants, such as CTAB ($CH_3(CH_2)_{15}N(Br)(CH_3)_3$), DTAB ($CH_3(CH_2)_{11}N(CH_3)_3Br$), and TTAB ($CH_3(CH_2)_{13}N(Br)(CH_3)_3$). Also, osmolytes (e.g., PEG Mw=8000 g/mol, Dextran Mw=155K g/mol). Unless otherwise indicated, Mw refers to weight average molecular weight.

Thus, In an infectious virus, packaged genome density and its ionic environment in the capsid are optimized. Even small perturbation of this optimum genome state, interferes with both genome ejection and packaging and consequently inhibits infectivity of the virion. The results of investigations on DNA packaging have implications with respect to the presence and the origin of a maximum length of DNA that can be packaged within a viral capsid. Indeed, longer DNA than wild-type (WT) genome length can be packaged. However, the rate of packaging, and thus the number of virions produced in a given time, decreases exponentially with increasing genome length. More precisely, a 1% increase in the length of the packaged genome above WT length leads to a 10-fold decrease in the viral titer. The maximum length of DNA that could be packaged in a virus is limited by the maximum force that the terminase motor can exert.

In the case of motor-driven genome packaging viruses such as phage λ and Herpes viruses, the packaging time becomes infinitely long as DNA length exceeds WT length, preventing viruses from assembling within reasonable time (or at all) to complete their replication cycle. This suggests that the length of the packaged genome has been evolutionarily optimized to packaging densities where the effect of salt on the motor efficiency is minimized, making packaging more robust and less prone to changes in the cellular environment. Most importantly, these findings demonstrate that slight changes in the internal pressure induced by variation in the DNA length will have fatal consequences for virus synthesis and the spread of infectious particles. This was demonstrated by the dramatic reduction in the number (efficiency) and size (rate) of plaques. These observations strengthen the role of internal pressure in the infectivity process, in agreement with several in vivo studies. This study also suggests new strategies for interfering with viral infectivity through small changes in the internal genome pressure in the case of motor-packaged DNA viruses (e.g. as we have shown, internal pressure can be increased or decreased by varying the ionic environment of encapsidated DNA by adding or removing cations).

DNA Solid-to-Fluid Transition in Viruses as a New Drug Target:

In one aspect, herpes DNA is packaged in a capsid to a crystalline density. The encapsidated DNA structure is trapped in a glassy state with restricted molecular motion between closely packed negatively charged DNA strands. It is demonstrated herein that this tight DNA confinement can strongly interfere with the initiation and initial translocation of genome from the viral capsid into the cell nucleus, strongly affecting the rate of herpes replication.

The mobility of the DNA in the Herpes capsid is increased and the interstrand sliding friction is minimized when herpesvirus is in ionic conditions similar to those of the epithelial or neuronal cell cytoplasm. Despite its tight packaging, the encapsidated herpes genome has a fluid-like structure under those ionic conditions. This is explained by the fact that monovalent and divalent cations present in the cytoplasm provide sufficient screening of negative charges on neighboring DNA helices, permitting less-restrained DNA motion. Furthermore, DNA strands can slide past each other without considerable electrostatic friction. However, it is also demonstrated that in the low-salt conditions occurring when divalent and polyvalent cations are removed from the viral host solution, the intracapsid DNA is rigid and has restricted mobility (see e.g., Sae-Ueng U., et al., "Solid-to-fluid DNA transition inside HSV-1 capsid close to the temperature of infection". Nature Chemical Biology, 7 Sep. 2014, 10, pgs. 861-867, incorporated herein by reference in its entirety). Therefore, by removing di- and polyvalent cations from encapsidated DNA, through addition of chelating agents, inhibits solid-to-fluid-like DNA transition in the capsid at physiologic temperature for infection (37° C.). This in turn inhibits viral infection.

According to one aspect of the invention, provided herein is a method of treating chickenpox. Chickenpox is caused by varicella-zoster virus (VZV) and includes symptoms such as a blister-like rash, itching, tiredness, and fever. The classic symptom of chickenpox is a rash that turns into itchy, fluid-filled blisters that eventually turn into scabs. Effective treatment of the chickenpox VZV viral infection includes, reduction and/or prevention of chickenpox symptoms, such as the rash and fever and additionally prevention of reoccurrence of chickenpox, such as in the form of shingles. The method comprises administering to a patient, e.g. topically to a chickenpox lesion (rash, scab, etc.), a compound or composition as described herein, e.g. comprising a polycationic polypeptide, a polycationic polymer, a DNA condensing protein, a cationic dendrimer, a branched polyamine, an inorganic cationic metal complex, a cationic surfactant, an osmolyte, and/or a chelating agent in an amount effective to inhibit release of the DNA from the capsid of the virus particle.

According to another aspect, provided herein is a method of treating CMV infection. Among other serious symptoms, CMV can cause vision impairment and/or hearing loss in neonates and immunosuppressed patients (e.g after organ transplant). 84% of US population has CMV which can activate when immune system is suppressed. In the method eye drops and/or ear drops are administered to a patient comprising a polycationic polypeptide, a polycationic polymer, a DNA condensing protein, a cationic dendrimer, a branched polyamine, an inorganic cationic metal complex, a cationic surfactant, an osmolyte, and/or a chelating agent in an amount effective to inhibit release of the DNA from the capsid of the virus particle, a compound. The eye drops and/or ear drops are optionally administered prophylactically after surgery for, e.g., organ transplant patients. Eighty four percent of US population has CMV which can activate when immune system is suppressed. In one aspect, this is a topical ointment or drops for the eye, prophylactically preventing permanent blindness caused by CMV damaging the optic nerve.

According to another aspect, provided herein is a method of treating shingles. Shingles is a reactivation of the varicella-zoster virus (VZV), which causes chickenpox. After having had chickenpox, the virus lies inactive in nerve tissue near the spinal cord and brain, and may be reactivated. Shingles is characterized by pain and a rash along a band of skin supplied by the affected nerve. Effective treatment of the shingles VZV viral infection includes, reduction and/or prevention of shingles symptoms, such as the rash, and additionally prevention of reoccurrence of shingles. The method comprises administering to a patient, e.g. topically to a shingles lesion (rash, scab, etc.), a compound or composition as described herein, e.g. comprising a polycationic polypeptide, a polycationic polymer, a DNA condensing protein, a branched polyamine, a cationic dendrimer, an inorganic cationic metal complex, a cationic surfactant, an osmolyte, and/or a chelating agent in an amount effective to inhibit release of the DNA from the capsid of the virus particle.

According to a further aspect, provided herein is a method of treating conditions caused by the herpes simplex virus (HSV). Infection with the herpes simplex virus, commonly known as herpes, can be due to either herpes simplex virus type 1 (HSV-1) or herpes simplex virus type 2 (HSV-2). HSV-1 is mainly transmitted by oral to oral contact to cause infection in or around the mouth (oral herpes). Symptoms of oral herpes include painful blisters or open sores called ulcers in or around the mouth. Sores on the lips are commonly referred to as "cold sores." HSV-1 can also cause ocular herpes. This type of herpes virus can cause inflammation and scarring of the cornea. HSV-2 is almost exclusively sexually transmitted, causing infection in the genital or anal area. Symptoms of HSV-2 are characterized by one or more genital or anal blisters or open sores called ulcers. In addition to genital ulcers, symptoms of new genital herpes infections often include fever, body aches, and swollen lymph nodes. Effective treatment of the HSV-1 or HSV-2 viral infections include, reduction and/or prevention of herpes-like symptoms, for example, for HSV-1, the reduction and/or prevention of cold sores, including the reoccurrence of cold sores, the reduction and/or prevention of inflammation and scarring of the cornea, including the prevention of reoccurrence of these symptoms. For HSV-2, the reduction and/or prevention of genital or anal blisters or open sores, and additionally the prevention of reoccurrence of these symptoms. The method comprises administering to a patient, e.g. topically to a herpes lesion (ulcer, sore, blister, etc.), a compound or composition as described herein, e.g. comprising a polycationic polypeptide, a polycationic polymer, a DNA condensing protein, a branched polyamine, a cationic dendrimer, an inorganic cationic metal complex, a cationic surfactant, an osmolyte, and/or a chelating agent in an amount effective to inhibit release of the DNA from the capsid of the virus particle.

Therefore, provided herein are methods of treating conditions caused by eukaryotic DNA viruses, such as conditions that are caused by Herpes simplex virus 1 (HSV-1), Herpes simplex virus 2 (HSV-2), Human cytomegalovirus (CMV), Varicella Zoster virus (VZV), Epstein Barr virus (EBV), Human herpes virus 6 (HHV-6), Human herpes virus 7 (HHV-7), Human herpes virus 8 (HHV-8) viruses. Specifically, provided herein is a method of reducing infectivity of a eukaryotic DNA virus, comprising contacting a eukaryotic DNA virus particle comprising DNA and a capsid with a composition comprising polycationic polypeptide, a polycationic polymer, a DNA condensing protein, a branched polyamine, a cationic dendrimer, an inorganic cationic metal complex, a cationic surfactant, an osmolyte, and/or a chelating agent in an amount effective to inhibit release of the DNA from the capsid of the virus particle.

In other words, provided herein are methods of treating conditions caused by eukaryotic DNA viruses by reducing the infectivity of a eukaryotic DNA virus. Reducing the infectivity of a eukaryotic DNA virus refers to methods that will reduce the release of dsDNA from the viral capsid or packaging of dsDNA into the viral capsid. As discussed above, maintaining the viral DNA in a more solid-like state will reduce mobility of the DNA and prevent the DNA from acquiring a fluid-like structure necessary for ejection from the viral capsid, which is a requirement for infectivity. Therefore, provided herein are methods for maintaining the viral DNA in solid-like state in order to reduce infectivity. For example, contacting a eukaryotic DNA virus particle with a composition comprising polycationic polypeptide, a polycationic polymer, a DNA condensing protein, a branched polyamine, a cationic dendrimer, an inorganic cationic metal complex, a cationic surfactant, an osmolyte, and/or a chelating agent, in order to alter pressure within the viral capsid and/or to vary ionic conditions. As discussed in detail above, variations in ionic conditions can restrict DNA mobility in the capsid, making it more solid-like. Moreover, reduction of pressure inside the virus will also reduce the ability of the intracapsid DNA from being ejected, thereby reducing infectivity. Further, low-salt conditions occurring when polyvalent ions are instead removed from the viral host solution results in increased rigidity and restricted mobility of the intracapsid DNA. This occurs due to increased electrostatic friction between closely packed negatively charged DNA strands in the capsid.

Figure 2:
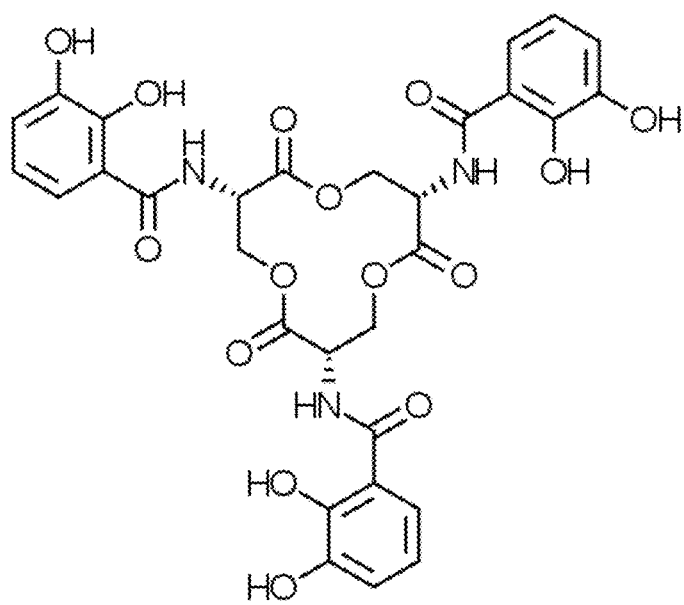
FIG. 2 provides a structure of enterobactin.

The data below shows that in the low-salt buffer, where $Mg^{2+}$ ions have been removed by addition of a chelating agent EDTA, the DNA ejection is essentially stalled by the rigid DNA state inside the capsid and no infection is observed. At the same time, in the high-salt buffer, where DNA mobility is higher, the ejection from all particles is completed in less than 10 minutes at room temperature. The kinetics data show that chelating agents can function as a drug molecule, binding the multivalent cations ions and preventing those ions from binding to the negatively changed packaged viral DNA. This leads to increased DNA-DNA electrostatic friction inside the capsid and inhibits the ability of Herpes virus to release its genome, making the virus non-infectious. These drug molecules include, but are not limited to EDTA (ethylene diamine tetra-acetic acid), EGTA (ethylene glycol tetraacetic acid), EDDA (ethylene diamine diorthohydroxyphenyl acetic acid), aminopolycarboxylic acids, DMPS (2,3-dimercapto-1-propanesulfonic acid), DMSA (dimercaptosuccinic acid or succimer). EDTA, DMPS and DMSA chelating agents are currently used in people for chelation therapy to remove toxic heavy metals. EDTA and DMPS are used intravenously, while DMSA has been used orally. Other examples of chelators include antibiotic drugs of the tetracycline and quinolone families, citric acid, and phosphonates. Another example is Enterobactin, produced by *E. coli*, is the strongest chelating agent known (FIG. 2).

Pharmaceutically acceptable salts of any of the compounds described herein also may be used in the methods described herein. Pharmaceutically acceptable salt forms of the compounds described herein may be prepared by conventional methods known in the pharmaceutical arts, and include as a class veterinarily acceptable salts. For example and without limitation, where a compound comprises a carboxylic acid group, a suitable salt thereof may be formed by reacting the compound with an appropriate base to provide the corresponding base addition salt. Non-limiting examples include: alkali metal hydroxides, such as potassium hydroxide, sodium hydroxide and lithium hydroxide; alkaline earth metal hydroxides, such as barium hydroxide and calcium hydroxide; alkali metal alkoxides, such as potassium ethanolate and sodium propanolate; and various organic bases such as piperidine, diethanolamine, and N-methylglutamine.

Acid and base addition salts may be prepared by contacting the free base form with a sufficient amount of a desired acid or base to produce the salt in a manner known in the art. The free base may be regenerated by contacting the salt form with a base or acid (depending on the nature of the salt) and isolating the free base. The free base forms differ from their respective salt forms somewhat in certain physical properties such as solubility in polar solvents, but otherwise the salts are equivalent to their respective free base forms for purposes described herein.

Compounds comprising basic nitrogen-containing groups may be quaternized with such agents as $C_{1-4}$ alkyl halides, such as methyl, ethyl, iso-propyl and tert-butyl chlorides, bromides and iodides; $C_{1-4}$ alkyl sulfate such as dimethyl, diethyl and diamyl sulfates; $C_{10-18}$ alkyl halides, such as decyl, dodecyl, lauryl, myristyl and stearyl chlorides, bromides and iodides; and aryl-$C_{1-4}$ alkyl halides, such as benzyl chloride and phenethyl bromide. Such salts permit the preparation of both water-soluble and oil-soluble compounds.

Non-limiting examples of pharmaceutically-acceptable base salts include: aluminum, ammonium, calcium, copper, ferric, ferrous, lithium, magnesium, manganic, manganous, potassium, sodium, and zinc salts. Salts derived from pharmaceutically acceptable organic non-toxic bases include, without limitation: salts of primary, secondary, and tertiary amines, substituted amines including naturally occurring substituted amines, cyclic amines, and basic ion exchange resins, such as arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine, and tris-(hydroxymethyl)-methylamine (tromethamine).

Acid addition salts may be prepared by treating a compound with pharmaceutically acceptable organic and inorganic acids, including, without limitation: hydrohalides, such as hydrochloride, hydrobromide, hydroiodide; other mineral acids and their corresponding salts such as sulfates, nitrates, and phosphates; alkyl- and mono-arylsulfonates, such as ethanesulfonate, toluenesulfonate, and benzenesulfonate; and other organic acids and their corresponding salts, such as acetate, tartrate, maleate, succinate, citrate, benzoate, salicylate, and ascorbate.

Non-limiting examples of pharmaceutically-acceptable acid salts include: acetate, adipate, alginate, arginate, aspartate, benzoate, besylate (benzenesulfonate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate, galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate, and phthalate.

Multiple salts forms are also considered to be pharmaceutically-acceptable salts. Common, non-limiting examples of multiple salt forms include: bitartrate, diacetate, difumarate, dimeglumine, diphosphate, disodium, and trihydrochloride.

As such, "pharmaceutically acceptable salt" as used herein is intended to mean an active ingredient (drug) comprising a salt form of any compound or composition as described herein. The salt form preferably confers to the improved and/or desirable pharmacokinetic/pharmodynamic properties of the compounds described herein.

In use, any compound described herein, including pharmaceutically acceptable salts thereof, may be admixed with any pharmaceutically acceptable carrier or carriers, such as water, saline, physiological salt solutions, Ringer's solution or any other carrier customarily used for administration of drugs to the subject in question (see, generally, Troy, D B, Editor, Remington: The Science and Practice of Pharmacy, 21st Ed., Lippincott Williams & Wilkins (2005), pp. 745-849 for descriptions of various compositions, solutions, and dosage forms useful for administration of the described compounds, as well as methods of making such compositions, solutions, and dosage forms).

According to one non-limiting example, the compounds described herein are formulated into a composition, such as a drug product with one or more additional pharmaceutically acceptable excipients, e.g., vehicles or diluents for oral, intravenous or subcutaneous administration. The composition can be formulated in a classical manner using solid or liquid vehicles, diluents and additives appropriate to the desired mode of administration. Orally, the compounds can be administered in the form of tablets, capsules, granules, powders and the like. The compositions optionally comprise one or more additional active agents, as are broadly known in the pharmaceutical, medicinal, veterinary or biological arts.

The compounds described herein may be administered in any manner that is effective to reduce the infectivity of a dsDNA virus, such as a herpesvirus, and therefore to treat or prevent recurrence of a viral disease caused by a dsDNA virus, such as a herpesvirus, thereby improving one or more symptoms, pathologies, sequelae, effects, etc. of the virus.

Examples of delivery routes include, without limitation: topical, for example, epicutaneous, inhalational, enema, ocular, otic and intranasal delivery; enteral, for example, orally, by gastric feeding tube or swallowing, and rectally; and parenteral, such as, intravenous, intraarterial, intramuscular, intracardiac, subcutaneous, intraosseous, intradermal, intrathecal, intraperitoneal, transdermal, iontophoretic, transmucosal, and epidural.

In use, according to one aspect of the invention, the composition administered topically, for example to a skin lesion (sore (e.g. cold sore), rash, vesicles, ulceration, wound, or other skin abnormality associated with a viral infection, such as a chickenpox rash, shingles, or a cold sore or ulceration of the skin or eye associated with HSV infection.

The compositions above, according to one aspect of the invention are combined with an antiviral agent suitable for treatment of an infection by a dsDNA virus, such as a herpesvirus. Suitable antiviral agents for treatment of herpesvirus infections include, without limitation: aciclovir, famciclovir, and valaciclovir.

Example 1

Materials and Methods
Phage λ and LamB Purification:
WT bacteriophage λ cI857, with a genome length of 48.5 kb was produced by thermal induction of lysogenic *E. coli* strain AE1 derived from the S2773 strain. Two phage λ mutants with shorter genome lengths (78 and 94% of the WT DNA length) were produced using a similar procedure. The receptor was the LamB protein purified from pop 154, a strain of *E. coli* K12 in which the LamB gene has been transduced from *Shigella sonnei* 3070. Phage and LamB purification details are described in Evilevitch A., et al., Osmotic pressure inhibition of DNA ejection from phage. Proc. Natl. Acad. Sci. U.S.A. 2003; 100:9292-9295 and Ivanovska I., et al., Internal DNA pressure modifies stability of WT phage. *Proc. Natl. Acad. Sci. U.S.A.* 2007; 104:9603-9608.

Isothermal Titration Calorimetry (ITC).

All calorimetric measurements were performed using the MicroCal iTC200 system manufactured by GE Healthcare, Life Sciences. The details of phage DNA ejection enthalpy measurements are described in Liu T., et al., Solid-to-fluid-like DNA transition in viruses facilitates infection. Proc. Natl. Acad. Sci. U.S.A. 2014; 111:14675-14680 and Jeembaeva M., et al., DNA heats up: energetics of genome ejection from phage revealed by isothermal titration calorimetry. J. Mol. Biol. 2010; 395:1079-1087.

Analysis of SAXS Measured DNA Diffraction Peak Position and Area.

Small angle X-ray scattering (SAXS) measurements were carried out at the 12-ID B station at the Advanced Photon Source at Argonne National Laboratory. A 12-KeV X-ray beam was used to illuminate the sample with an overall scattering vector q range from 0.006 to 0.850 Å−1. A total of 120 μl of phage solution (~5×10¹³ pfu/ml) was injected into a flow-through glass capillary and the solution was oscillated during the SAXS measurement with a flow rate of 10 μl/s. Forty scans with 1 s X-ray exposure time were collected and averaged for each sample. A buffer solution of the dialysis buffer for phage samples was measured using the same SAXS setup, which was further subtracted as the background. After the background subtraction, the scattered intensity I versus q was plotted and the DNA peak region was truncated from 0.18 Å−1 to 0.33 Å−1. This DNA diffraction peak was fitted with a Gaussian curve plus a linear background using function (1), where $q_0$ is the peak center, w is the peak width, $A_0$ is the peak area, k is the slope of the linear background and c is the offset.

$$I = \left(\frac{A_0}{w \times \sqrt{\pi/2}}\right) e^{-\left(\frac{q-q_0}{w}\right)} + kq + c \qquad (1)$$

The DNA peak area $A_0$ was chosen as the most convenient measure of the ordered DNA strands, because it includes a temperature factor or the displacement parameter, which signifies the drop in the diffraction peak intensity due to the thermally induced vibration or displacement of the scattering centers. Further details are provided in Liu T., et al., Solid-to-fluid-like DNA transition in viruses facilitates infection. Proc. Natl. Acad. Sci. U.S.A. 2014; 111:14675-14680.

Single-Molecule Fluorescence Measurements of Phage Ejection Ensemble Kinetics.

Phage particles were imaged using a Nikon 2000E2 microscope with a spinning disk confocal scan head (Yokagawa Industries, Tokyo, Japan).

Results

Effect of ionic conditions on DNA transition temperature. While variation in the monovalent ion concentration has a small influence on intra-capsid DNA stress, polyvalent cations present in the bacterial cytoplasm, such as polyamines and $Mg^{2+}$, have been shown to have a strong effect on the repulsive interactions between packaged DNA helices. Since the free polyamine concentration in cells is very low as most polyamines are bound to cellular DNA and RNA we were specifically interested in the effect of the Mg-ion concentration on the DNA transition temperature in phage λ at concentrations similar to those of extra- and intracellular $Mg^{2+}$ in vivo.

Mg-concentration not only affects DNA stress in the capsid, it also strongly influences the transition temperature of the encapsidated genome (Liu T., et al., Solid-to-fluid-like DNA transition in viruses facilitates infection. Proc. Natl. Acad. Sci. U.S.A. 2014; 111:14675-14680). Therefore, it was investigated whether physiologic Mg-concentrations provide optimum conditions for phage λ infectivity in vivo by facilitating DNA transition in the k capsid close to the temperature of infection (37° C.). Such a unique correlation between the Mg-concentration and DNA transition temperature would suggest that the intracapsid DNA transition is an important regulatory mechanism for viral replication.

Figure 3A:
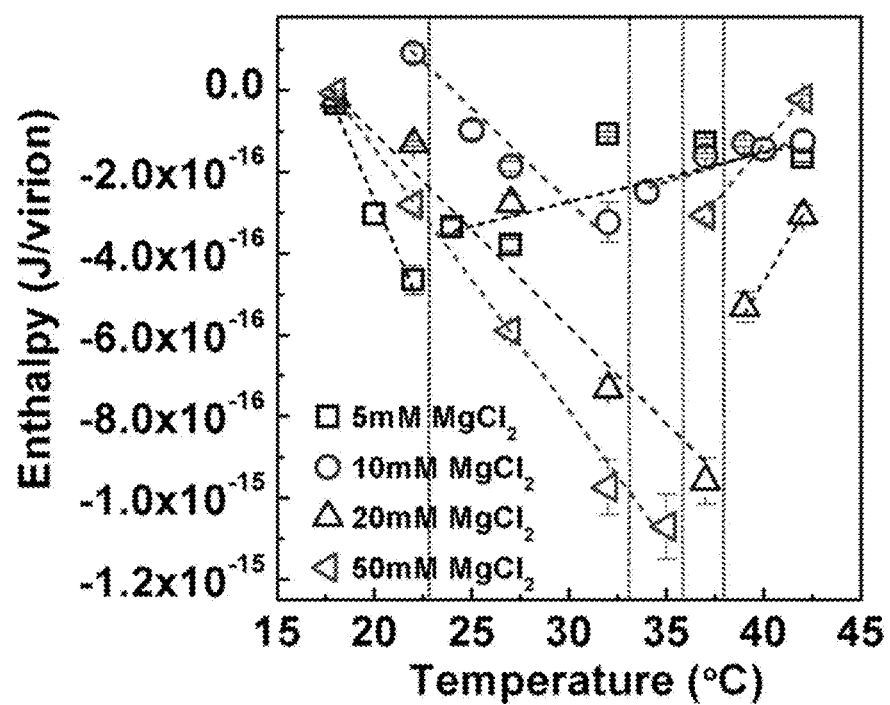
FIGS. 3A-3C.
Figure 3B:
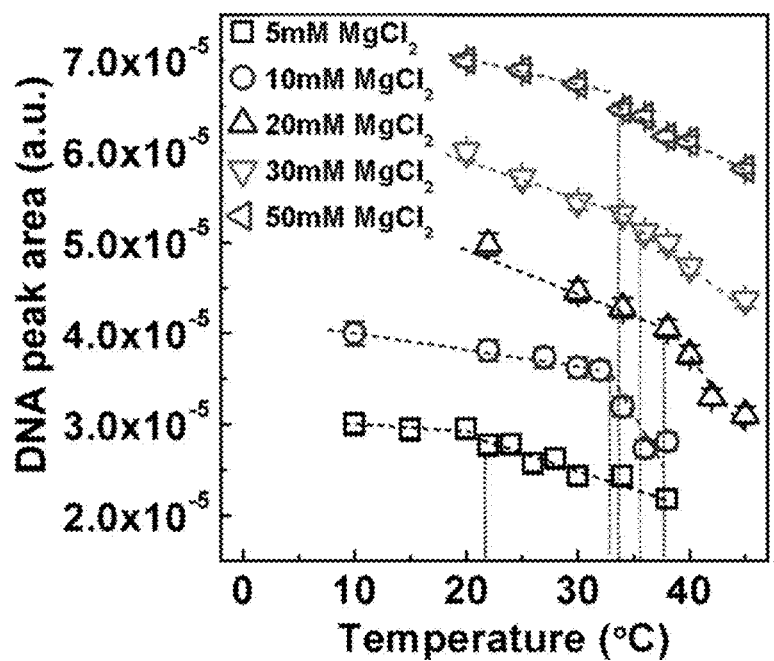
Figure 3C:
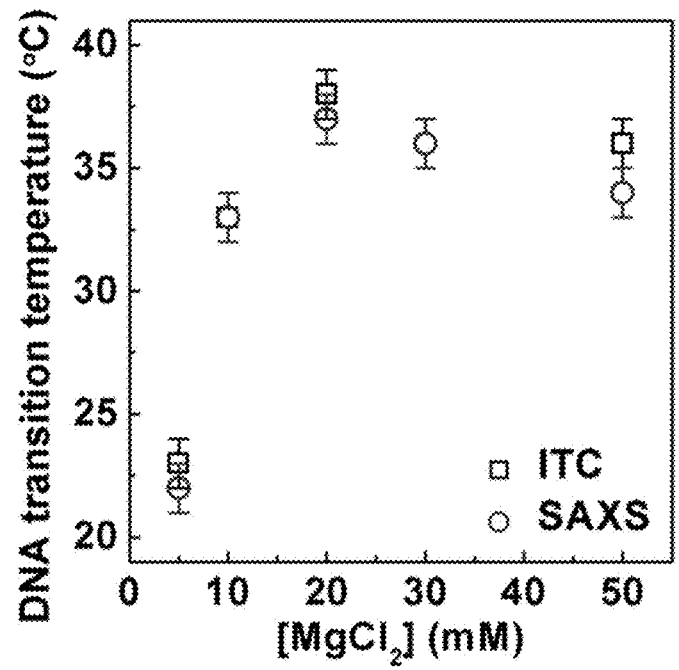

ITC and SAXS assays were used to determine DNA transition temperatures for WT k-DNA length phage in $MgCl_2$ Tris-buffer with $MgCl_2$ concentrations varied between 5 and 50 mM, see FIGS. 3A-3C. The intracapsid DNA transition occurs at temperature T*, corresponding to either a discontinuity in the linear dependence of $\Delta H_{ej}$ on temperature (FIG. 3A) or to an abrupt change in the linear decay of the DNA diffraction peak area versus temperature measured by SAXS (FIG. 3B). DNA transition temperatures as a function of Mg-concentration determined by both techniques are in good agreement with each other and are summarized in FIG. 3C. Increasing the Mg-concentration will initially significantly reduce the strength of the interstrand repulsive interactions in the capsid due to the counterion screening of the negative charges between packaged DNA helices. However, the inventors have previously shown that at DNA packing density in phage λ, the screening effect of Mg-ions will become progressively smaller with increasing Mg-concentration due to the counter-ion saturation (Evilevitch A., et al., Effects of salt concentrations and bending energy on the extent of ejection of phage genomes. Biophys. J. 2008; 94:1110-1120). Furthermore, if the Mg ion concentration continues to increase, the counterions are forced into regions on the helices that begin to increase the effective repulsions between packaged DNA strands. Thus, there is a minimum in interstrand repulsive interaction versus Mg-concentration (Evilevitch A., et al., Effects of salt concentrations and bending energy on the extent of ejection of phage genomes. Biophys. J. 2008; 94:1110-1120; and Yang J., et al., Incomplete ion dissociation underlies the weakened attraction between DNA helices at high spermidine concentrations. Biophys. J. 2005; 89:1932-1940).

FIG. 3C shows that the DNA transition temperature T* is at first significantly increased with increasing Mg-concentration, from T*~22° C. at 5 mM $MgCl_2$ Tris-buffer to T*~37° C. at 20 mM $MgCl_2$ Tris-buffer. However, increasing the Mg-concentration further has an opposite effect on the DNA transition temperature, showing a weak decrease in T* between 20 and 50 mM $MgCl_2$. T* reaches ~35° C. at 50 mM $MgCl_2$, see FIG. 3C. This variation in the transition temperature correlates well with previously observed non-monotonic variation in the DNA stress in the capsid with increasing Mg-concentration (Evilevitch A., Fang L. T., Yoffe A. M., Castelnovo M., Rau D. C., Parsegian V. A., Gelbart W. M., Knobler C. M. Effects of salt concentrations and bending energy on the extent of ejection of phage genomes. Biophys. J. 2008; 94:1110-1120), as described above. Initially, as the Mg-concentration is increased between 5 and 20 mM, the internal DNA stress is reduced leading to a higher transition temperature. That is, a higher temperature is required to reach the critical DNA stress limit in order to overcome the energetic barrier triggering the structural genome transition. Once the $Mg^{2+}$-ion saturation yielding maximum counterion screening between the packaged DNA helices occurs at ~20 mM (Evilevitch A., et al., Effects of salt concentrations and bending energy on the extent of ejection of phage genomes. Biophys. J. 2008; 94:1110-1120), the interstrand repulsive interactions start to increase again with increasing Mg-concentration. This results in a decrease of T*, since the critical intracapsid DNA stress level required for transition is now achieved at a lower temperature. Thus, while T* varies significantly with $Mg^{2+}$ concentration, the most favorable Mg-concentration for E. coli growth (McCarthy B. J. The effects of magnesium starvation on the ribosome content of Escherichia coli. Biochim. Biophys. Acta. 1962; 55:880-889) and for phage λ infection of E. coli (~10-20 mM) (Fry B. A. Conditions for the infection of Escherichia coli with lambda phage and for the establishment of lysogeny. J. Gen. Mmicrobiol. 1959; 21:676-684) triggers DNA transition in the capsid precisely at the physiologic temperature of infection (~37° C.). This striking correlation confirms our assumption, namely, that the intracapsid DNA transition mechanism in λ is evolutionarily adapted to both the ionic environment and temperature of its host, suggesting its significance for viral replication.

Switching Intracapsid DNA Transition on and Off:

Intercapsid DNA transition is triggered by temperature increase. However, DNA in the capsid has to reach a critical stress value at the transition temperature (T*) before the encapsidated DNA can undergo the transition from being in a solid state to a fluid-like state. The overall stress can be varied in turn by packaged DNA length or by polyvalent cations diffusing into the capsid and affecting the interstrand repulsive interactions. It was observed that varying either of these two parameters leads to variation in the internal DNA stress and transition temperature. This suggests that the intracapsid DNA transition can be switched on and off for the same viral particle within the physiologically relevant temperature range studied here (10-45° C.). To demonstrate this assumption, 78 and 100% WT DNA length phage λ in 10 mM $MgCl_2$ Tris-buffer were selected as reference systems. The 78% WT DNA length λ does not display an intracapsid DNA transition, while 100% WT DNA length phage λ undergoes a DNA transition at ~33° C. (Li D., et al., Ionic switch controls the DNA state in phage λ. Nucleic Acids Research, 2015, pgs. 1-11).

Figure 4A:
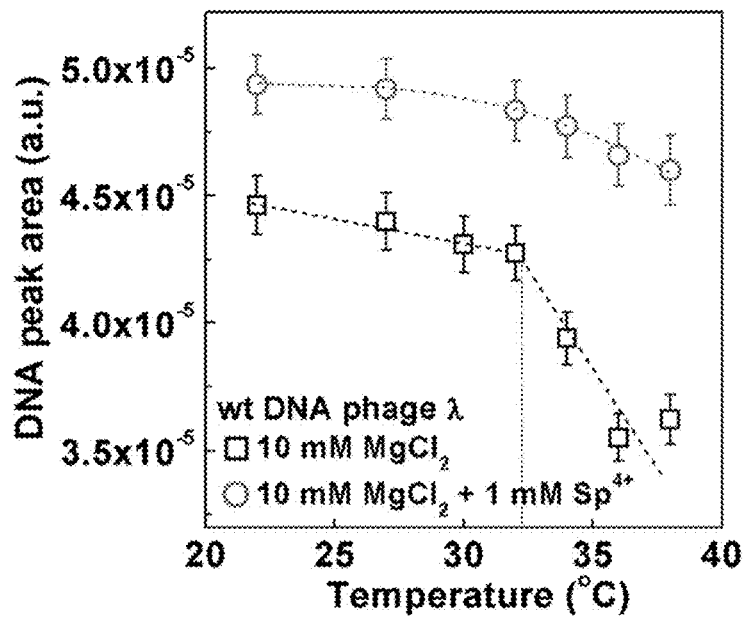
FIGS. 4A-4C.

In the first set of measurements, 1 mM of spermine (4+) ions was added to the WT DNA length phage λ to introduce attractive interactions between packaged DNA strands (Lander G. C., et al., DNA bending-induced phase transition of encapsidated genome in phage lambda. *Nucleic Acids Res.* 2013; 41:4518-4524; Evilevitch A., et al., Effects of salt concentrations and bending energy on the extent of ejection of phage genomes. Biophys. J. 2008; 94:1110-1120; and Rau D. C., et al., Direct measurement of temperature-dependent solvation forces between DNA double helices. *Biophys. J.* 1992; 61:260-271). This allows re-establishing of interstrand packing defects (that were hindered by the increased temperature) and reduces the overall DNA stress. The DNA diffraction peak area now shows only slight variation in the entire temperature range (20-40° C.), and no abrupt DNA transition is observed, in contrast to WT DNA phage λ without added spermine (4+), see FIG. 4A. Thus, the DNA transition in the capsid has been switched off with spermine (4+) ions, where the increasing DNA repulsive interactions with increasing temperature (resulting from hindering of the packing defects) are now offset by the spermine (4+) induced attractive interactions. The DNA stress in the capsid is therefore insufficient for DNA transition to occur.

Figure 4B:
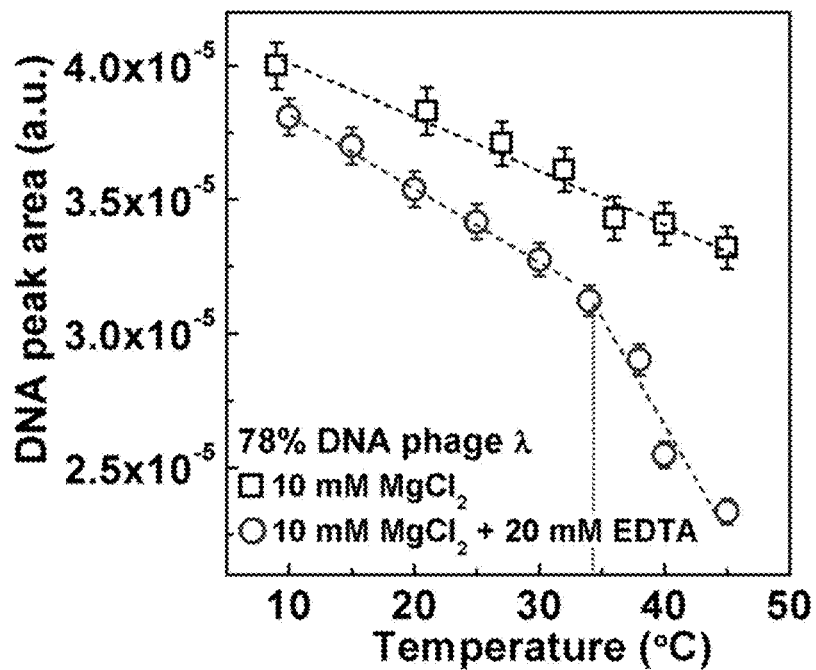
Figure 4C:
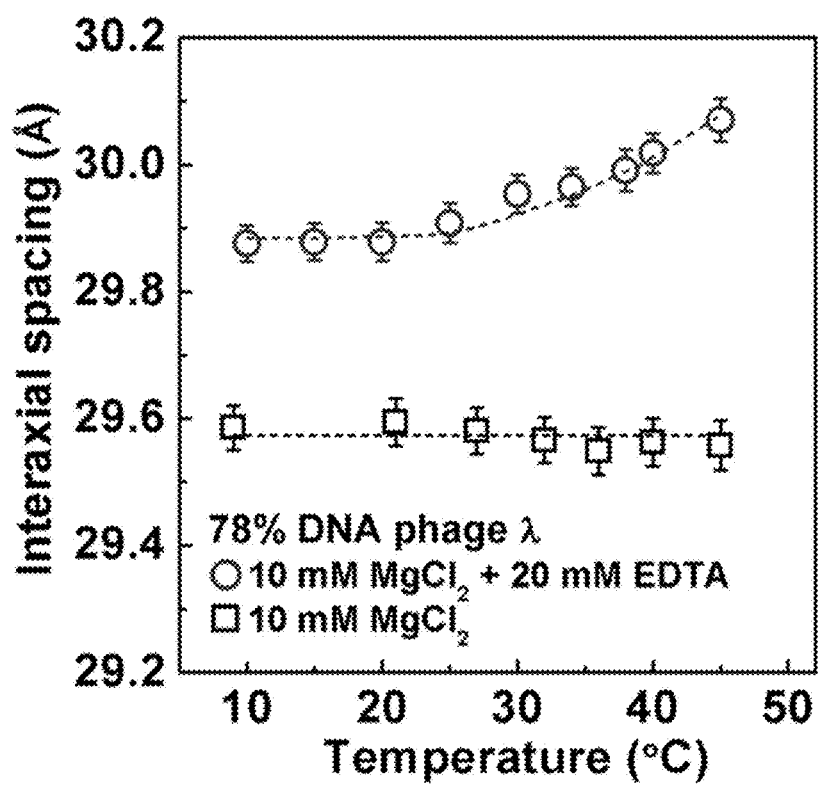

Next, it was determined whether DNA transition can instead be switched on in the 78% WT DNA length phage λ. 78% WT DNA length phage λ in 10 mM $MgCl_2$ Tris-buffer does not display a DNA transition between 10 and 40° C. due to insufficient DNA stress in the capsid, (Li D., et al., Ionic switch controls the DNA state in phage λ. *Nucleic Acids Research*, 2015, pgs. 1-11). Through addition of excess ethylenediaminetetraacetic acid (EDTA), Mg-ions are chelated (20 mM EDTA added to 10 mM $MgCl_2$ Tris-buffer solution), which increases repulsion between packaged DNA strands and leads to a higher DNA stress in the capsid. This increase in DNA stress in the 78% WT DNA length phage λ appears to be sufficient to trigger DNA transition at T*~36° C. FIG. 4B shows the DNA diffraction peak area versus temperature for 78% WT DNA length phage λ with and without EDTA. There is an abrupt drop in the DNA peak area when EDTA is added, demonstrating a DNA disordering transition. Based upon these results, it can be concluded that DNA transition in a viral capsid can be switched on and off by varying the polyvalent counterion concentration, which affects the repulsive interactions between packaged genome strands.

Example 2—Testing of Chelating and Condensing Compounds

The following describes exemplary chelators and condensing agents for use in the methods described herein, along with exemplary useful concentration ranges and exemplary, theoretically optimal concentrations. Included are and pharmaceutically acceptable salts of any of the following. Initially, the antiviral activity of the following compounds will be tested on HSV-1, HSV-2, CMV, and VZV, and later on EBV, HHV-6, HHV-8, and KSV.

Chelating Agents
a. EDTA disodium salt (Ethylenediaminetetraacetic acid, Sigma-Aldrich, $C_{10}H_{16}N_2O_8$); Molecular weight: 372.2 Da; PSA: 156 $Å^2$; LD50: 4500 mg/kg (~15 mM); Suggested concentration range: 0.016 mM-50 mM;
b. EGTA (Ethylene glycol-bis(2-aminoethylether)-N,N,N',N'-tetraacetic acid, Sigma-Aldrich, $C_{14}H_{24}N_2O_{10}$); Molecular weight: 380.3 Da; PSA: 174 $Å^2$; LD50: 3587 mg/kg (~9.5 mM); Suggested concentration range: 0.016 mM-50 mM;
c. EDDA (Ethylenediamine-N,N'-diacetic acid, Sigma-Aldrich, $C_6H_{12}N_2O_4$); Molecular weight: 176.2 Da; PSA: 176 $Å^2$; LD50 unknown; Suggested concentration range: 0.016 mM-50 mM;
d. DMSA (meso-2,3-Dimercaptosuccinic acid, Sigma-Aldrich, $C_4H_6O_4S_2$); Molecular weight: 182.2 Da; PSA: 76.6 $Å^2$; LD50: 5011 mg/kg (~27.5 mM); Suggested concentration range: 0.016 mM-50 mM; and
e. DMPS (Sodium 2,3-dimercaptopropanesulfonate monohydrate, Sigma-Aldrich, $C_3H_7NaO_3S_3$); Molecular weight: 210.3 Da; PSA: 67.6 $Å^2$; LD50 unknown; Suggested concentration range: 0.016 mM-50 mM.

Naturally Occurring Protamines (Condensing Agents)
a. spermine tetrahydrochloride (Sigma-Aldrich, $C_{10}H_{30}C_{14}N_4$); Charge: 4+; Molecular weight: 348.2 Da (parent compound spermine MW=202.3 Da); PSA: 76.1 $Å^2$; LD50—oral (rat)=129 mg/kg (~0.4 mM);

DNA condensation observed experimentally (Todd, B. A., et al. (2008). "Attractive forces between cation condensed DNA double helices." *Biophys J* 94(12): 4775-4782; DeRouchey, J., et al. (2010). "Cation charge dependence of the forces driving DNA assembly." *Biophys J* 99(8): 2608-2615; and DeRouchey, J., B. et al. (2013). "A comparison of DNA compaction by arginine and lysine peptides: a physical basis for arginine rich protamines." *Biochemistry* 52(17): 3000-3009), $d_{int}$=28 Å, Internal experimental observations: $d_{int}$=28.2-29.4 Å for 0.5-100 mM; Optimal concentration: CA/P~35 (0.004 µM at $10^6$ pfu/mL); suggested concentration range for $10^6$ pfu/mL: 0.00032-1.0 µM; and b. Spermidine trihydrochloride (Sigma-Aldrich, $C_7H_{22}C_{13}N_3$); Charge: 3+; Molecular weight: 254.6 Da; PSA: 64.1 Å$^2$; LD50 unknown; DNA condensation observed experimentally (Rau, D. C. et al. (1992). "Direct measurement of the intermolecular forces between counterion-condensed DNA double helices." *Biophys J* 61: 246-259; Todd, B. A., et al. (2008). *Biophys J* 94(12): 4775-4782; and DeRouchey, J., et al. (2010). *Biophys J* 99(8): 2608-2615), $d_{int}$=28.8-29.7 Å; Optimal concentration: CA/P~2.5 (0.0004 µM at $10^6$ pfu/mL); Suggested concentration range for $10^6$ pfu/mL: 0.00016-0.5 µM.

c. protamine sulfate, e.g., protamine sulfate salt from salmon (salmine).

Synthesized cationic polypeptides (condensing agents) (repeating linear or branched chains of polycationic amino acids), commercially available, or custom synthesized from GenScript Corporation. Examples include poly-L-arginine (e.g., Arg3+, Arg4+, Arg5+, Arg6+, Arg7+, Arg8+), poly-L-lysine (e.g., Lys3+, Lys4+, Lys5+, Lys6+, Lys7+, and Lys8+), co-poly(L-Lys L-Arg), e.g., $Lys_3Arg_3$, or $(LysArg)_3$, and polyornithine (e.g., Orn3+, Orn4+, Orn5+, etc.).

a. Arg3+(Charge=+3; MW=468.6 Da; dint=30.1 Å); DNA condensation observed experimentally (DeRouchey, J., et al. (2010). *Biophys J* 99(8): 2608-2615 and An, M., et al. (2014). "Intermolecular forces between low generation PAMAM dendrimer condensed DNA helices: role of cation architecture." *Soft Matter* 10(4): 590-599), $d_{int}$=30.1 Å, Optimal concentration; CA/P~2.5 (0.0004 µM at $10^6$ pfu/mL); Suggested concentration range for $10^6$ pfu/mL: 0.00016-0.5 µM;

b. Arg4+(Charge=+4; MW=642.8 Da; $d_{int}$=29.8 Å); DNA condensation observed experimentally (DeRouchey, J., et al. (2010). *Biophys J* 99(8): 2608-2615 and An, M., et al. (2014). *Soft Matter* 10(4): 590-599): $d_{int}$=29.8 Å, Internal observations: $d_{int}$=29.7-30.3Å for 1-2.5 mM; Optimal concentration: CA/P~2.5 (0.0003 µM at $10^6$ pfu/mL); Suggested concentration range for $10^6$ pfu/mL: 0.00016-0.5 µM;

c. Trilysine (Sigma-Aldrich, $C_{18}H_{38}N_6O_4$). Charge: +3; Molecular weight: 402.5 Da; PSA: 200 Å$^2$; LD50 unknown; DNA condensation observed experimentally: (DeRouchey, J., B. et al. (2013). *Biochemistry* 52(17): 3000-3009); $d_{int}$=38.9 Å; Optimal concentration: CA/P~5 (0.0008 µM at $10^6$ pfu/mL); Suggested concentration range for $10^6$ pfu/mL: 0.00016-0.5 µM;

d. Tetralysine (Lys4+, Sigma-Aldrich); Charge=+4; Molecular Weight=530.7 Da; PSA: 255 Å$_2$; LD50 unknown; DNA condensation observed experimentally (DeRouchey, J., B. et al. (2013). *Biochemistry* 52(17): 3000-3009): $d_{int}$=34.9 Å; Optimal concentration: CA/P~5 (0.0006 µM at $10^6$ pfu/mL); Suggested concentration range for $10^6$ pfu/mL: 0.00016-0.5 µM;

e. Triornithine ($C_{15}H_{32}N_6O_4$); Charge=+3; Molecular weight=360.5 Da; PSA: 200 Å$^2$; LD50 unknown; DNA condensation observed experimentally (DeRouchey, J., B. et al. (2013). *Biochemistry* 52(17): 3000-3009), $d_{int}$=35.6 Å; Optimal concentration: CA/P~5 (0.0008 µM at $10^6$ pfu/mL); Suggested concentration range for $10^6$ pfu/mL: 0.00016-0.5 µM; and f. Tetraornithine; Charge=+4; Molecular weight~474.6 Da; PSA~250 Å$^2$; LD50 unknown; DNA condensation observed experimentally (DeRouchey, J., B. et al. (2013). *Biochemistry* 52(17): 3000-3009), $d_{int}$=32.2 Å; Optimal concentration: CA/P~5 (0.0006 µM at 106 pfu/mL); Suggested concentration range for $10^6$ pfu/mL: 0.00016-0.5 µM.

DNA Condensing Proteins a. Histone proteins (Linker: H1; Core: H2A, H2B, H3, H4), or b. Transition nuclear proteins (TP1 and TP2).

Cationic Dendrimers a. PAMAM G0 (PAMAM dendrimer, ethylenediamine core, generation 0.0 solution, Sigma-Aldrich, $C_{22}H_{48}N_{10}O_4$); Charge=+4; Molecular weight=516.7 Da; PSA: 227 Å$^2$; LD50 unknown; DNA condensation observed experimentally (An, M., et al. (2014). *Soft Matter* 10(4): 590-599), $d_{int}$=31 Å, Internal observations: $d_{int}$=32-35.2 Å, for 0.15-2.50 mM; Optimal concentration: CA/P~4 (0.0005 µM at $10^6$ pfu/mL); Suggested concentration range for $10^6$ pfu/mL: 0.00016-0.5 µM;

Branched Polyamines a. Branched polyethylenimine (Oakwood Chemical, bPEI MW 600, $C_{24}H_{63}N_{13}$); Charge=+6; Molecular weight=533.8 Da; PSA: 205 Å$^2$; LD50 rat: 500-2000 mg/kg (~1-4 mM); DNA condensation observed experimentally (DeRouchey, J., et al. (2005). "Structural investigations of DNA-polycation complexes." *Eur Phys J E Soft Matter* 16(1): 17-28), dint=26.6 Å, Internal experimental observations: dint=28.2 Å for 0.006-0.5 mM; Optimal concentration: CA/P~1.5 (0.0006 µM at $10^6$ pfu/mL); Suggested concentration range for $10^6$ pfu/mL: 0.00016-0.5 µM.

Inorganic Cations a. Hexaamminecobalt(III) chloride ($C_{13}CoH_{18}N_6$); Charge=+3; Molecular weight=267.5; PSA=6 Å$^2$; LD50 unknown; DNA condensation observed experimentally (Rau, D. C. et al. (1992). "Direct measurement of temperature-dependent solvation forces between DNA double helices." *Biophys J* 61: 260-271; Rau, D. C. et al. (1992). *Biophys J* 61: 246-259; and Todd, B. A., et al. (2008). *Biophys J* 94(12): 4775-4782), $d_{int}$=27.8-28.2 Å, Internal experimental observations: DNA condensed to 28 Å, 2-100 mM; Optimal concentration: CA/P~15 (0.003 µM at $10^6$ pfu/mL); Suggested concentration range for $10^6$ pfu/mL: 0.00032-1 µM.

Cationic Surfactants a. CTAB (Sigma-Aldrich, hexadecyltrimethylammonium bromide, $CH_3(CH_2)_{15}N(Br)(CH_3)_3$); Charge: +1, but able to aggregate into highly charged micelles; Molecular weight=364.4 Da; PSA=0 Å$_2$; LD50—rat: 410 mg/kg (~1.1 mM), CAC=0.6 mM, CMC=5.2 mM (Chatterjee, A., et al. (2002). "Studies on surfactant-biopolymer interaction. I." *Biophys Chem* 93: 313-327); Optimal concentration: between CAC and CMC (e.g. 1 mM); Suggested concentration range: 0.32-1000 µM;

b. DTAB (dodecyltrimethylammonium bromide, Sigma-Aldrich); Charge: +1, but able to aggregate into highly charged micelles; Molecular weight=308.3 Da; PSA=0 $Å^2$; LD50—rat: 200-1000 mg/kg (~0.6-3.2 mM); CAC=0.9 mM, CMC=15 mM (Guillott, S., et al. (2003). "Polyelectrolytesurfactant complexes at interaces and in bulk." *J. Phys. Condens. Matter* 15: S219-S224); Optimal concentration: between CAC and CMC (e.g. 2 mM); Suggested concentration range: 0.0096-30 mM; and c. TTAB (myristyltrimethylammonium bromide, Sigma-Aldrich); Charge: +1, but able to aggregate into highly charged micelles; Molecular weight=336.4 Da; PSA=0 $Å^2$; LD50—rat: 3900 mg/kg (~11.6 mM); CAC=0.05 mM (Corbyn, C. P., et al. (2009). "Re-dissolution and de-compaction of DNA-cationic surfactant complexes using non-ionic surfactants." *Phys Chem Chem Phys* 11(48): 11568-11576), CMC=3 mM (Morel, G., et al. (1991). "Enhanced nitrate ultrafiltration by cationic surfactant." *J. Mem. Sci.* 56: 1-12); Optimal concentration: between CAC and CMC (e.g., 1.5 mM); Suggested concentration range: 0.0032-10 mM.

Osmolytes a. PEG8000 $(H(OCH_2CH_2)_nOH)$; Molecular weight: 8000 Da; PSA: 5220 $Å^2$ (estimated from ethylene glycol monomer PSA of 40.5 $Å^2$); LD50: >50,000 mg/kg (~6.25M); Optimal concentration: 37.5 mM; Suggested concentration range: 0.016 mM-50 mM.

Methods:

The following assays were previously used to study the antiviral activity of various nucleosides (see, Prichard, M. N., et al. (2013) Synthesis and Antiviral Activities of Methylenecyclopropane Analogs with 6-Alkoxy and 6-Alkylthio Substitutions That Exhibit Broad-Spectrum Antiviral Activity against Human Herpesviruses, *Antimicrobial Agents and Chemotherapy* 57(8):3518-3527).

Cells culture and virus strains. Human foreskin fibroblast (HFF) cells prepared from human foreskin tissue. The tissue is incubated at 4° C. for 4 h in Clinical Medium consisting of minimum essential media (MEM) with Earl's salts supplemented with 10% fetal bovine serum (FBS) (Hyclone, Inc. Logan Utah), L-glutamine, fungizone, and vancomycin. Tissue is then placed in phosphate buffered saline (PBS), minced, rinsed to remove the red blood cells, and resuspended in trypsin/EDTA solution. The tissue suspension is incubated at 37° C. and gently agitated to disperse the cells, which are collected by centrifugation. Cells are resuspended in 4 ml Clinical Medium and placed in a 25 $cm^2$ flask and incubated at 37° C. in a humidified $CO_2$ incubator for 24 h. The media is then replaced with fresh Clinical Medium and the cell growth is monitored daily until a confluent monolayer has formed. The HFF cells are then expanded through serial passages in standard growth medium of MEM with Earl's salts supplemented with 10% FBS, L-glutamine, penicillin, and gentamycin. The cells are passaged routinely and used for assays at or below passage 10 (Prichard M N, et al., Activity and mechanism of action of N-methanocarbathymidine against herpesvirus and orthopoxvirus infections. Antimicrob Agents Chemother. 2006; 50(4):1336-41). COS7 cells are obtained from ATCC.

Lymphocytes are maintained routinely in RPMI 1640 (Mediatech, Inc., Herndon, Va.) with 10% FBS, L-glutamine and antibiotics and passaged twice a week, as described previously (Prichard M N, et al., A rapid DNA hybridization assay for the evaluation of antiviral compounds against Epstein-Barr virus. *J Virol Methods.* 2007; 144(1-2):86-90 and Prichard M N, et al., Benzimidazole analogs inhibit human herpesvirus 6. *Antimicrob Agents Chemother.* 2011; 55(5):2442-5). The construction of RC314 with a K355M mutation in the UL97 kinase is reported previously (Gill R B, et al., Conserved retinoblastoma protein-binding motif in human cytomegalovirus UL97 kinase minimally impacts viral replication but affects susceptibility to maribavir. Virol J. 2009; 6:9).

Antiviral Assays:

Each experiment that evaluated the antiviral activity of the compounds included both positive and negative control compounds to ensure the performance of each assay. Concurrent assessment of cytotoxicity is also performed for each study (see below).

Plaque Reduction Assays for HSV-1, HSV-2, VZV, and HCMV.

Monolayers of HFF cells are prepared in six-well plates and incubated at 37° C. for 2 d to allow the cells to reach confluency. Media is then aspirated from the wells and 0.2 ml of virus is added to each of three wells to yield 20-30 plaques in each well. The virus is allowed to adsorb to the cells for 1 h and the plates are agitated every 15 minutes. Compounds are diluted in assay media consisting of MEM with Earl's salts supplemented with 2% FBS, L-glutamine, penicillin, and gentamycin. Solutions ranging from 300 μM to 0.1 μM are added to duplicate wells and the plates are incubated for various times, depending on the virus used. For HSV-1 and -2, the monolayers are then stained with 1% crystal violet in 20% methanol and the unbound dye removed by washing with $dH_2O$. For all other assays, the cell monolayer is stained with 1% Neutral Red solution for 4 h then the stain is aspirated and the cells are washed with PBS. For all assays, plaques are enumerated using a stereomicroscope and the concentration of compound that reduced plaque formation by 50% ($EC_{50}$) is interpolated from the experimental data.

DNA Hybridization Assays for EBV, HHV-6A, and HHV-6B.

Assays for EBV are performed in Akata cells that are induced to undergo a lytic infection with 50 μg/ml of a goat anti-human IgG antibody by methods we reported previously (Prichard M N, et al., *J Virol Methods.* 2007; 144(1-2):86-90). Experimental compounds are diluted in round bottom 96-well plates to yield concentrations ranging from 20 to 0.0064 μM. Akata cells are added to the plates at a concentration of $4 \times 10^4$ cells per well and incubated for 72 h. For HHV-6 assays, compounds are serially diluted in 96-well plates then $1 \times 10^4$ uninfected HSB-2 or Molt-3 cells are added to each well. Infection is initiated by adding HHV-6A infected HSB-2 cells, or HHV-6B infected Molt-3 cells, at a ratio of approximately 1 infected cell for every 10 uninfected HSB-2 cells or Molt-3 cells respectively. Assay plates are incubated for seven days at 37° C.

For all assays, 100 μl of denaturation buffer (1.2M NaOH, 4.5M 80 NaCl) is added to each well to denature the DNA and a 50 μl aliquot is aspirated through an Immobilon nylon membrane (Millipore, Bedford, Mass.) using a Biodot apparatus (Bio-Rad, Hercules, Calif.). The membranes are then allowed to dry before equilibration in DIG Easy Hyb (Roche Diagnostics, Indianapolis, Ind.) at 56° C. for 30 min. Specific digoxigenin (DIG)-labeled probes are prepared fore each virus according to the manufacturer's protocol (Roche Diagnostics). For EBV, primers 5'-CCC AGG AGT CCC AGT AGT CA-3' and 5'-CAG TTC CTC GCCTTAG-GTTG-3 amplified a fragment corresponding to coordinates 96802-97234 in EBV genome (AJ507799). A specific HHV-6 DIG labeled probe is prepared using primers 5'-CCT TGA TCA TTC GAC CGT TT-3' and 5'-TGG GAT TGG GAT TAG AGC TG-3' to amplify a segment of ORF2 (coordinates 37820-38418 in X83413). Membranes with EBV DNA are hybridized overnight at 56° C. followed by sequential washes 0.2×SSC with 0.1% SDS and 0.1×SSC with 0.1% SDS at the same temperature. For HHV-6A and HHV-6B blots, the probe is allowed to hybridize overnight at 42° C. and the blots are rinsed at the same temperature with 0.2×SSC with 0.1% SDS and 0.1×SSC with 0.1% SDS. Detection of specifically bound DIG probe is performed with anti-DIG antibody using the manufacturer's protocol (Roche Diagnostics). An image of the photographic film is captured and quantified with QuantityOne software (Bio-Rad) and compound concentrations sufficient to reduce the accumulation of viral DNA by 50% ($EC^{50}$), are interpolated from the experimental data.

DNA Hybridization Assays for HHV-8.

For primary assays, test compounds are diluted in duplicate wells of a 96-well plate with the highest final concentration of 60 µM. BCBL-1 cells at a concentration of 2×10$^4$ cells/well are then added to the wells containing the compounds and then the cells are induced to undergo a lytic infection by the addition of phorbol 12-myristate 13-acetate (Promega, Madison Wis.) at a final concentration of 100 ng/ml. For secondary assays, test compounds are diluted in triplicate wells of a 96-well plate with the highest final concentration of 100 µM. BCBL-1 cells are induced to undergo a lytic infection by the addition of phorbol 12-myristate 13-acetate (Promega, Madison Wis.) at a final concentration of 100 ng/ml and incubated for 2 h. Induced cells at a concentration of 2×10$^4$ cells/well are added to each well in the plate. For both assays, induced cells are incubated for 7 days at 37° C. in a humidified $CO_2$ incubator then total DNA is prepared with a Wizard SV 96 well purification kit (Promega)., and viral DNA is quantified by real time PCR using forward primer 5'-TTC CCC AGA TAC ACG ACA GAA TC-3', reverse primer 5'-CGG AGC GCA GGC TAC CT-3', and probe 5'-(FAM) CCT ACG TGT TCG TCG AC (TAMRA)-3'. Plasmid pMP218 containing a DNA sequences corresponding to nucleotides 14120-14182 (AF148805.2) is used to provide absolute quantification of viral DNA. Compound concentrations sufficient to reduce genome copy number by 50% are calculated from experimental data.

Cytotoxicity Assays:

Every antiviral assay includes a parallel cytotoxicity assay with the same cells used for each virus, the same cell number, the same drug concentrations, and the same incubation times to provide the same drug exposure. To ensure that the cytotoxicity of all compounds is compared directly, a standard neutral red uptake cytotoxicity assay is performed for all compounds in confluent HFF cells with a 7 day incubation period.

Neutral Red Uptake Cytotoxicity Assays.

Each compound is evaluated in a standard cytotoxicity assay by standard methods (Prichard M N, et al., *Antimicrob Agents Chemother.* 2006; 50(4):1336-41). Briefly, HFF cells are seeded into 96-well tissue culture plates at a 2.5×10$^4$ cells/well in standard growth medium. After 24 h of incubation, medium is replaced with MEM containing 2% FBS, and compounds are added to the first row and then 5-fold serial dilutes are used to generate a series of compound concentrations with a maximum of 300 µM. Assay plates are then incubated for 7 days, and 100 µl of a 0.66 mg/ml neutral red solution in PBS is added to each well and the plates incubated for 1 h. The stain is then removed, the plates rinsed with PBS and the dye internalized by viable cells is solubilized in PBS supplemented with 50% ethanol and 1% glacial acetic acid. The optical density is then determined at 550 nm and $CC_{50}$ values are interpolated from the experimental data.

For all plaque reduction assays, cytotoxicity assays are performed on a parallel set of 6-well plates containing HFF cells that received the same compound concentrations as used for the antiviral assays, but remained uninfected. For HSV-1 and HSV-2, monolayers are stained with crystal violet as described above and the monolayers are inspected visually for signs of cytotoxicity. For all other plaque assays, the cytotoxicity plates are removed from the incubator on the same day as each antiviral assay and the cell monolayer is stained for 6 h with 2 ml of a neutral red solution at a concentration of 0.165 mg/ml in PBS. The dye is then removed, residual dye rinsed from the cells with PBS, and cell monolayers are inspected visually for any signs of toxicity.

Cytotoxicity in Lymphocyte Assays.

Cell viability in all assays with lymphocytes is assessed with the CellTiter-Glo Luminescent Cell Viability Assay (Promega) by established methods (Prichard M N, et al., *J Virol Methods.* 2007; 144(1-2):86-90). Briefly, assay plates are incubated at ambient temperature for 30 min then 50 µl of CellTiter-Glo reagent is added to each well and the plates are mixed for 2 min on an orbital shaker to lyse the cells. Plates are then incubated for an additional 10 min at ambient temperature and the luminescence is quantified on a luminometer. Standard methods are used to calculate drug concentrations that inhibited the proliferation of Akata, HSB-2, BCLB-1, or Molt-3 cells by 50% ($CC_{50}$).

Cell Proliferation Assays.

The inhibition of HFF cell proliferation is used to refine estimates of cytotoxicity for some compounds and is performed according to a standard procedure used in the laboratory (Prichard M N, et al. Inhibition of herpesvirus replication by 5-substituted 4'-thiopyrimidine nucleosides. Antimicrob Agents Chemother. 2009; 53(12):5251-8). Cells are seeded at a low density into six-well plates using 2.5×10$^4$ cells/well and standard culture medium. After 24 h, the medium is aspirated, and a range of compound solutions in the growth medium is prepared starting at 300 µM, and added to duplicate wells. The plates are incubated for 72 h at 37° C., the cells are then dislodged with trypsin and counted on a Beckman Coulter Counter. Compound concentrations that reduced cell proliferation by 50% are interpolated from experimental data.

Example 3

We tested the role of osmotic pressure in viral DNA ejection in a reconstituted system made of isolated rat liver nuclei, cytosolic mixture and purified HSV-1 capsids. The reconstituted solution system encompassed the necessary and sufficient components for efficient HSV-1 DNA ejection into nucleus. This system was placed at physiological temperature (37° C.) for half an hour, then DNA samples from nucleoplasm, nuclei-bound capsids, free capsids and extranuclear fluid were separately extracted and assayed by quantitative PCR analysis for HSV-1 DNA contents. Both iso-osmotic (no external osmolyte added) and hyper-osmotic (with external osmolyte added) buffer conditions were tested using this system to demonstrate an osmotic suppression of DNA ejection from HSV-1 into a nucleus. We found that in iso-osmotic conditions, an average of 98.3% of the nuclei-bound capsids have ejected their DNA into the nucleoplasm. When increasing the osmotic pressure to 18 atm through addition of 30% polyethylene glycol (PEG)

with molecular weight 8000 g/mol (PEG-8k) to the solution, the percentage of ejecting, nuclei-bound capsids reduced to 0.2%. This striking result directly shows the key role of external osmotic pressure on DNA ejection into nucleus. Furthermore, it also provides the first demonstration that pressurized DNA state in HSV-1 capsid is responsible for DNA release into a cell nucleus. We also examined the role of osmolarity on DNA ejection by supplement of a different osmolyte, dextran with molecular weight of 155k g/mol (Dextran-155k). We confirmed that the suppression of DNA ejection depends on the external osmotic pressure only and not on the chemical nature of the osmolyte. These results provide the first experimental evidence of viral DNA translocation from Herpesviruses, driven by a mechanical pressure, into a reconstituted nucleus system in a cellular environment.

Materials and Methods

HSV-1 Capsid, Rat Liver Nuclei Isolation, BHK Cytosol Prep.

Purification of HSV-1 capsids were described previously (D. W. Bauer, J. B. Huffman, F. L. Homa, A. Evilevitch, Herpes virus genome, the pressure is on, *J Am Chem Soc*, 135 (2013) 11216-11221). African green monkey kidney cells (Vero) were infected with HSV-1 KOS strain or HSV-1 (Kos)-RFP (HSV-1 KOS virus that expresses RFP conjugated to the capsid protein VP26) at a multiplicity of infection (MOI) of 5 pfu/cell for 20 h at 37° C. Cells were collected, pelleted and resuspended in 20 mM Tris buffer (pH 7.5) on ice for 20 min and lysed by addition of 1.25% (v/v) Triton X-100 (Alfa Aesar) for 30 min on ice. Lysed cells were centrifuged at 2000 rpm for 10 min and the nuclei pellets were resuspended with 1× protease inhibitor cocktail (Complete; Roche) added. Nuclei were disrupted by sonication for 30 s and loaded onto TNE sucrose gradient at 24 k rpm for 1 h. The C-capsid band was isolated by side puncture, diluted in TNE buffer and centrifuged at 24 k rpm for an additional 1 h. Capsids were resuspended in a preferred capsid binding buffer (CBB: 20 mM HEPES-KOH with pH of 7.3, 80 mM K-acetate, 2 mM DTT, 1 mM EGTA, 2 mM Mg-acetate, 1 mM PMSF, and 1× CLAP cocktail).

Nuclei from rat liver were isolated as adapted from previously described protocol. Livers were chopped, grinded then fileted through a metal mesh in 0.25M STKM buffer (0.25 M sucrose, 25 mM HEPES-KOH pH 7.4.25 mM KOAc, 5 mM $MgCl_2$, 0.1 mM EDTA, 1 mM PMSF, 1× CLAP cocktail and 1 mM DTT). Samples were treated by centrifugation at 1000 g for 10 min and resuspended in 0.25 M STKM solution with 1× protease inhibitor cocktail (complete; Roche). The pellets were then homogenized 20 times using a Dounce homogenizer on ice. The homogenate was centrifuged at 1000 g for 10 min at 4° C.

Nuclei pellets were resuspended in 0.25M STKM buffer and mixed with approximately double volume 2.3 M STKM buffer to raise the sucrose concentration to 1.6M. Nuclei were then separated from the cytoplasmic components by underlaying the homogenate with 2.3 M STKM buffer followed by centrifugation in a Beckman 5W28 rotor at 25 k rpm for 40 min at 4° C. The white nuclear pellets were harvested and resuspended in 0.25 M STKM and re-homogenized with Dounce for 3 strokes. Homogenate were underplayed with 30% STKM and centrifugated at 2000 rpm for 10 min. Pellets were resuspended in 0.25 M STKM, pelleted and frozen in liquid nitrogen and store at −80° C. for long term storage.

The cytosol was separately prepared using BHK-21 cells (ATCC CCL-10). Cells were grown to confluent in 245×245 mm plates and collected from the plates by addition of 0.25% trypsin/EDTA (ThermoFisher Scientific). Collected cells were washed with KEHM buffer (50 mM KCl, 10 mM EGTA, 50 mM Herpes, pH 7.4, 2 mM MgCl2) and kept on ice. Cells were then resuspended in KEHM buffer supplement with 1 mM DTT and 1× protease inhibitor (complete; Roche) at the volume of 5 mL KEHM per 109 cells. Resuspended cells were broken using EMBL 8.020 mm cell cracker homogenizer with ball sizes 8.010, 8.008 or 8.004 nm, then spin at 3000 rpm, 4° C. for 15 min to remove the intact cells and nuclei. The supernatant was re-spin at 80,000 rpm (267,000 g), 4° C. for 30 min and only the supernatant was kept as the purified cytosol. The cytosol was frozen in liquid nitrogen and store at 80° C. for long time storage.

Reconstituted Nuclei-Capsid System.

An in vitro viral HSV-1 DNA translocation system was built in which HSV-1 genome was released into nucleoplasm in a homogenate solution mimicking cytoplasm environment. In a typical 500 μL scale system, 8×105 counts of rat liver cell nuclei was incubated with approximately 109 counts of viruses on ice for 10 min in CBB buffer as previously described [10] containing: (i) BHK cell cytosol (final concentration reading about 2.5 mg/mL protein contents) (ii) 1 mg/mL BSA (iii) ATP regeneration system composed of 5 mM creatine phosphate (Sigma), 20 U of creatine phosphokinase (Sigma), 1 mM ATP, 0.2 mM GTP. Then osmolytic solution of PEG-8k (or water in control sample) was added to make up a total of 500 μL system. Final osmolytes in the solution reaches a concentration of 30% w/w. The system is incubated 37° C. for 30 min then transferred on ice for a minimum of 10 min.

Fluorescence Imaging.

For fluorescence microscopy, both unlabeled and the RFP-labeled HSV-1 capsids were used. For unlabeled HSV-1 C-capsid, it is prestained by YOYO-1 iodide (ThermoFisher Scientific). After incubation as described, the buffer system containing purified HSV capsids and nuclei were loaded onto cover-slips. For RFP-capsid incubation, 1000× diluted Syto13 were added to stain viral and nuclear DNA [15]. For YOYO-1 stained c-capsids incubation, Hoechst 33342 (ThermoFisher Scientific) were used nuclear DNA. Overlay of the confocal 488 (for syto13 emitted signal) and 560 (for RFP emitted signal) channels show the localization of viral capsid onto the nucleus. For estimating of total viral number attached to nuclei, a z-stack were done through the nuclear volume and 3-D reconstruction of the nuclei were done by Imaris.

Electron Microscopy.

After nuclei-capsid binding incubation as described earlier, the samples were washed once with CBB buffer at 1000 rpm for 5 min, then fixed with 2% gluteraldehyde in phosphate buffered saline (PBS) 1 to 3 hr, followed by 1 hr incubation with 1% osmium tetroxide in PBS. Samples were dehydrated by a graded ethanol series and propylene oxide, embedded in Epon, and further contrasted with lead citrate and uranyl acetate.

Capsid Pull-Down Assay.

After capsid-nuclei incubation, the system was centrifuged at 3k rpm to spin down the capsid-associated nuclei. Nuclei pellet was washed twice in CBB buffer at 4° C. to remove excessive osmolytes in the pellet (low temperature and placement of the sample on ice at all times were required to minimize DNA ejections after the incubation stage). The pellet was then resuspended and incubated for 20 min in 1× reticulocyte standard buffer (RSB: 10 mM Tris of pH 7.5, 10 mM KCl, 1.5 mM MgCl2, 0.5% NP-40 substitute) for nuclear membrane lysis. The supernatant was collected separately as the extranuclear solution.

Both extra-nuclear supernatant solution and lysed nuclear pellet were then incubated with 5 μL anti-HSV1/2 ICP5/UL19 antibody for overnight at 4° C. 500 μL 50% Protein A bead slurry (Sigma-Aldrich P1406) was added to each samples to capture viral capsid-antibody complex on the next day. Protein A bead complex was collected by low speed centrifugation (1500 rpm, 5 min). The supernatant was collected as capsid-free part (sample b and d in FIG. 3). In parallel, the pelleted beads parts were re-suspended in Proteinase K solution to digest the capsid and let viral DNA diffuse into the solution (sample a and c in FIG. 3). Then all the sample solutions were phenol-chloroform treated and DNA was ethanol precipitated at re-suspended in clean water.

This in vitro assay successfully parted HSV-1 DNA into four samples: (a) HSV genome from those capsids unbound or failed to dock onto nuclear pore complex. (b) Free HSV DNA in the extra-nuclear solution due to contamination or broken capsids. (c) HSV DNAs still sustained inside the nuclear-associated capsids within the time frame of experimental incubation. (d) HSV genomes that are successfully ejected into nucleoplasm.

Quantification of each part of traces of viral genome in the in vitro translocation system was crucial to understand the efficiency of viral genome release in our reconstructed system. Extracted DNAs from sample a, b, c, d were quantified by real-time PCR analysis for DNA level by custom TaqMan assays. Viral genes VP16 and ICP0 were quantified with primers and probe sequences. The assays were performed using a StepOnePlus system (Applied Biosystems) and were analyzed with software provided by the supplier. Viral gene copies were calculated with comparison to amplification from HSV-1 DNA with known copy numbers.

Results

HSV-1 C-Capsids Docking to NPC.

A cell-free system was reconstituted to mimic the in vivo HSV-1 DNA ejection into nucleus inside the cytoplasm. Purified nuclear C-capsids were incubated with isolated rat liver nuclei, in presence of BHK cell cytosol. To maximize HSV-1 binding events per nuclei, C-capsids were added in abundance relative to nuclei (~1200:1 ratio). Importin β was the only cytosolic factor known to be sufficient and necessary for HSV-1 capsid binding, depletion of Importin β result in inhibition of nuclei binding events. Here, no purified importin β was separately appended; thus the cytosol homogenate was a critical component for the capsid-binding assay. In addition, a creatine phosphokinase (CPK), phospho-creatine (PC) based ATP-regeneration system was supplemented to the system. Although binding of the HSV-1 capsids to nuclei was found to be independent of energy in the form of ATP, the subsequent DNA ejection step was found to be ATP-dependent. Supplementation of ATP-regeneration system was shown to enhance the DNA ejection efficiency about three-fold.

Tegument proteins were implicated to be critical for nuclear trafficking (interaction with the dynein motor), docking and binding. After HSV cell-entry, some of the capsid-associated tegument proteins were released into the peripheral cytoplasm while others remain tightly attached. Removal of teguments, either by mild trypsinization or by microinjection of specific tegument protein VP1/2 (UL36) antibodies show reduced level of HSV-1 binding. However in our system, we allow for a 30-40 min incubation time frame for capsids binding, we found that using un-tegumented C-capsids are sufficient for our assay. Later confirmed by qPCR results, more than 90% of the C-capsids in the system are, or have been nuclei-bound (FIG. 5).

Figure 6:
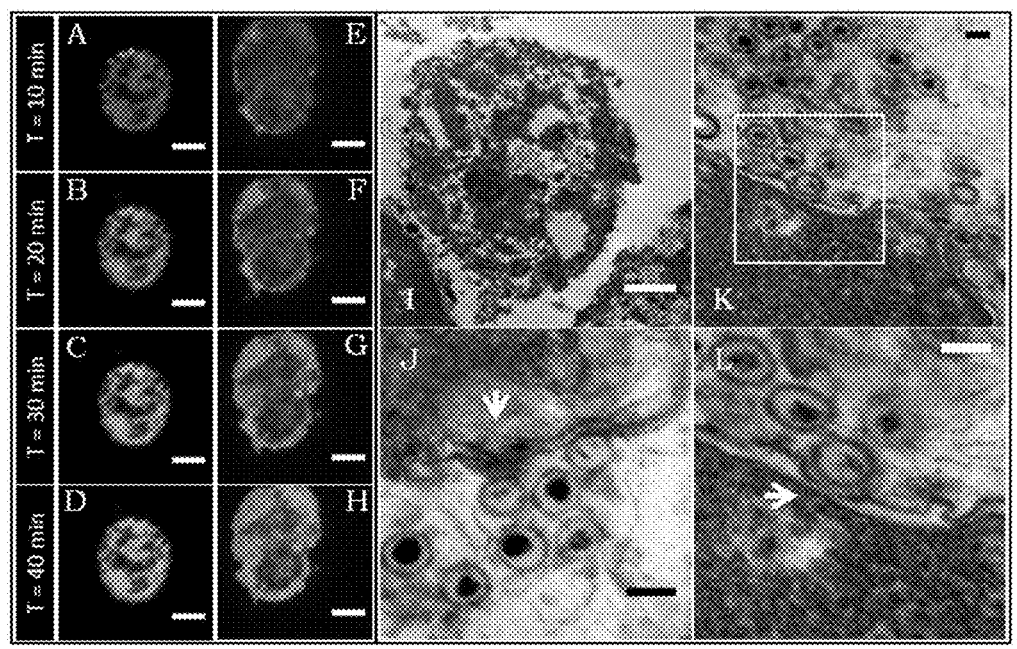
FIG. 6: HSV C-caspids docking to nucleus, observed both by fluorescence and electron microscopy. All fluorescence images were obtained by spinning disk confocal microscopy, nuclei DNA stained by Hoechst (blue in original) and capsid DNA labeled by YOYO-1 (green in original). Columns (A) through (D), (E) through (H) are two different examples. Each nuclei sample was pre-incubated with HSV-1 capsids for 10 min before imaging, so T starts at 10 min. (I) through (L) are the electron microscopy observation of our incubation system. (I) shows the full view of a nuclei bound with many viruses on its surface (J) is the zoom in of the nuclei membrane where an empty capsid bound to NPC is clearly visible here (indicated by arrow head). We can see some DNA-filled, non-ejected capsids around competing for the binding locations on a nuclear membrane. (K) Another view of capsids associated with nuclear membrane, (L) A "zoom in" of the boxed region in (K), nuclear pore structure indicated by an arrow. Scale bar, (A-H): 5 μm. (I): 1 μm (J-L): 100 nm.

Previous in vitro HSV-1 binding assay indicate optimized binding condition for capsid-nuclei at 37° C. for 40 min (P. M. Ojala, et al. Herpes simplex virus type 1 entry into host cells: reconstitution of capsid binding and uncoating at the nuclear pore complex in vitro, Molecular and cellular biology, 20 (2000) 4922-4931). We observed efficient capsid docking events onto nuclear membrane as early as 10 min and within 40 min, nuclear surfaces were majorly covered with C-capsid signal (FIG. 6, panel A-F). To help visualization, our C-capsids were labeled with YOYO-1 DNA dye. One drawback using DNA dye is that these dye molecules would stain nuclear DNA as well. Localization of these dye molecules inside the nucleus (FIG. 6, panel D, H) may either come from ejected viral DNA or freshly stained heterochromatin DNA.

In the assay, the purified C-capsids were pre-stained in YOYO-1, then washed 2-3 times to get rid of the additional dye in the capsid buffer before incubation with the nuclei. YOYO-1 is a DNA intercalation dye, and dissociation half time for similar dyes was found on tens of ms (millisecond) scale. Which means upon bathing with nuclei, there will always be free YOYO dyes available in the buffer, which came off from the capsid DNA. These free YOYO dyes have a greater tendency to stain the less-packaged heterochromatin DNA. Though the binding of YOYO to the nucleus is much more time-consuming. The intercalation time constant for free YOYO-1 in the range of our assay was measured to be longer than 5 min. Shown in the fluorescence imaging results, the gradual appearance of YOYO signal in the nucleoplasm in a visible level starts at about 30 min post-incubation. And by T=40 min, roughly half of nucleoplasm were stained by YOYO-1, indicated by co-localization with Hoechst dye.

EM imaging of our in vitro HSV-nucleus system confirms that bound capsids are docked onto the NPC structure on the nuclear membrane (FIG. 6 I-L). In EM studies, we observed a layer of capsids in proximity of the nuclear membrane (FIGS. 6I and H) since no strict stripping of unbound capsids were done for EM sample preparation. EM samples require maximized nuclei preservation, compared to fluorescence imaging, in which less rigorous standards of the nuclei are for imaging purposes thus we can apply excessive washing to remove all the unbound capsids from proximity of the nucleus. Shown in EM, most NPC-docked capsids are empty after 30 min incubation time while the unbound capsids in proximity remains DNA filled (FIG. 6 I-J). Dense patches of heterochromatin are normally seen all over the inner membrane side except around the NPC to leave a "pathway" for nuclear transport. Positions of NPC were confirmed in our EM images by association with absence of heterochromatin on the nucleoplasm side (FIG. 6 K-L).

The fluorescence imaging result in FIG. 6, panels A-H shows good binding statistics of C-capsids to nucleus, though counting individual capsids are un-achievable with YOYO-stained capsids, especially when they start to stain the chromatin DNA In mammalian cells. Number of pore complexes on the nuclear membrane ranges anywhere from 1000 to 5000 per nucleus depending on the cellular type, which all could be potential sites for capsid binding. Additionally, after nuclear docking and DNA ejection, empty capsids were eventually released back into cytosol, leaving new available sites for capsid binding. The good binding statistics was later confirmed by quantitative PCR (qPCR) results, more than 90% of the C-capsids in our reconstituted system were shown to be, or have been nuclei-bound (Table 1). The fact that most of the capsids are associated with nuclear membrane is likely due to time scale of the experiment, where in fluorescence and electron microscopy, only one time-point was recorded. However all the capsids that have ejected DNAs into the nucleoplasm within the whole incubation time frame was recorded by non-imaging method.

To better visualize individual capsids on the nuclei, we later used C-capsids purified an HSV-1-KOS strain with small capsid protein VP26 tagged with RFP. Unfortunately, these capsids were displayed a significant reduction in binding capacity to nuclei (FIG. 6 M-R). VP26 was shown to mediate HSV-1 capsid binding to cytoplasmic dynein, thus critical for nuclear localization. However in our cell-free bathing system, cytoskeleton plays a minimum role in capsid localization. One HSV-1 capsid can harbor up to 900 copies of VP26 as it decorates on the tip of every hexons, protrusions of RFP protein everywhere on the capsid surface may have well interfered with the binding capacity to the nucleus through a none-specific interaction mechanism. We observed in each confocal cross-section, there is consistently 2 to 6 DNA filled capsids bind to each nuclei (FIG. 6, panel O—R). 3D reconstruction from continuous confocal slices estimated an average total of 30 to 50 RFP-capsids per nuclei (FIGS. 6M and N). These results unfortunately do not reflect true binding statistics of non-RFP labeled capsids (which we used for the quantification assay) as discussed.

Nuclear Morphology and Integrity in Hyper-Osmotic Conditions.

Figure 7:
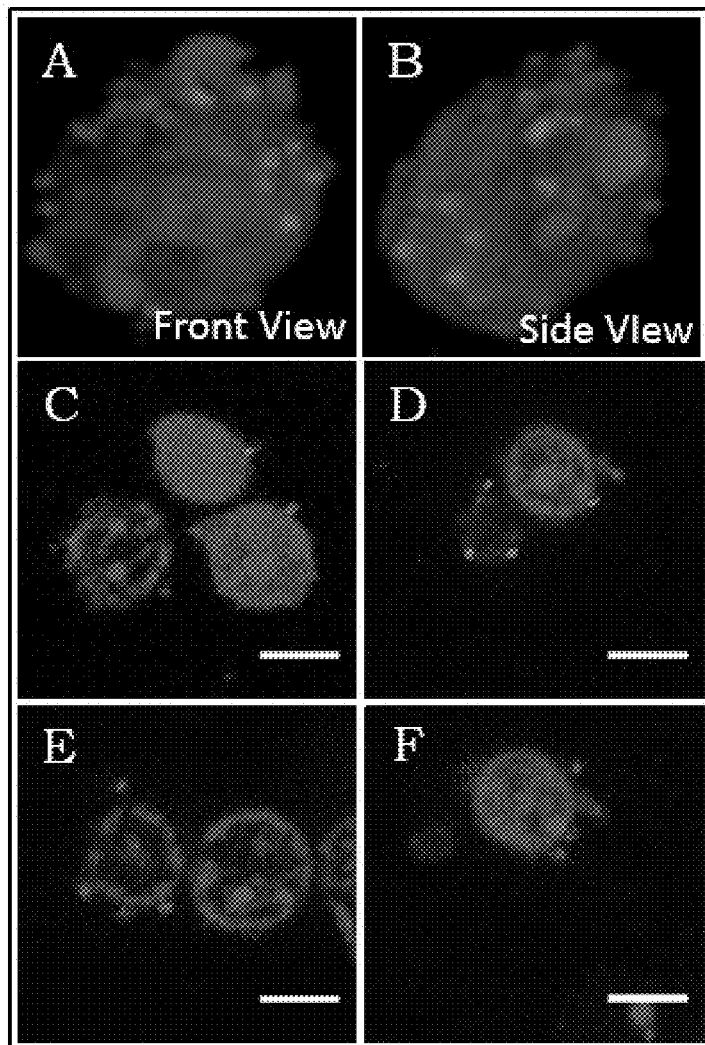
FIG. 7: HSV RFP-labeled C-capsids binding to nucleus, observed by confocal fluorescence microscopy. Nuclei DNA stained by Syto13 (green in original) and viral capsids labeled by RFP (red in original). (A) and (B) shows the 3D reconstruction of capsids-bound nuclei from confocal slices scanning through the whole nucleus volume in z-directions. (A): front (B): side view of the same nucleus. (C) through (F) are confocal z-sections of nuclei. Scale bar in (C—F): 5 μm.

Now that we verified in our reconstructed cell-free system, viral capsids can successfully dock onto NPC on the nuclear membrane. We next confirmed that the nucleus remains in biologically competent condition upon addition of osmolytes. FIG. 2 shows nuclei retained their morphology under osmotic pressure by PEG-8k or Dextran-155k. The interior of nuclei remains intact and structured, seen by differential interference contrast microscopy (DIC, first row panel in FIG. 7). The total number of good nuclei remains unchanged as well (data not shown). The sub-nuclear structure of heterochromatin DNA was essentially unchanged upon addition of osmolytes, as visualized by Hoechst stain (second row panel in FIG. 7). However we observed a slight shrink in nuclear size with presence of increasing osmolytes concentration. Studies show under hyper-osmotic stress, the nucleus size shrinks and assumes a more convoluted shape. In the hyper-osmotic range, the nucleus volume decrease in a linear pattern with decreased inverse normalized osmolarity. Previous results also indicate under hyper-osmotic conditions, distribution of Hoechst dye would become more heterogeneous due to altering in chromatin condensation. In our experimental condition, the change in distribution of Hoechst dye was not observable.

Osmotic pressure was know to play a role on nucleus transport, under hyper-osmotic stress, the rate of nuclear transport increased using passive diffusing nuclear cargo. Further studies show this rate change was mainly due to the decrease in the nuclear volume, resulting in a shorter effective diffusion distance. The nuclear permeability remains unchanged up to 480 mOsm. For our 30% PEG-8k (w/w) solution, osmolarity is around 38.5 mOsm and for 30% Dextran-155k (w/w) solution, osmolarity is around 1.9 mOsm. This confirmation of nuclei integrity and functionality with addition of osmolytes is critical for our next step in the assay to monitor DNA ejection into nucleus under osmotic pressure.

Quantification of Viral DNA Traces in the Reconstituted System.

Figure 8:
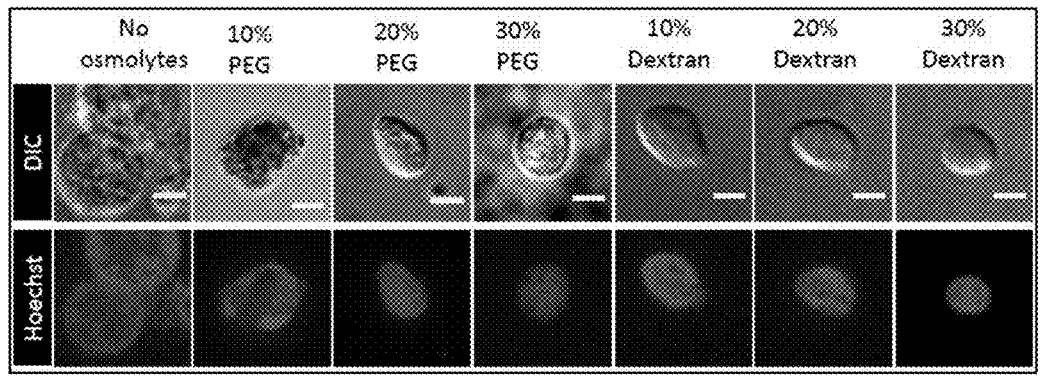
FIG. 8: Control of external osmotic pressure effect on nuclei morphology. Nuclei suspended in CBB buffer with 0%-30% osmolytes (PEG-8k or Dextran-155k) in surrounding solution. Nuclei were imaged by DIC shown in first row, we can see the nuclei morphology remained unchanged up to 30% Dextran. Nuclear DNA was stained by Hoechst 33342 and shown in the second row of images. Scale bar in all images is 3 μm.

Next, we quantified the capsid binding and DNA ejection efficiency, with being capable to track all traces of viral DNA in the reconstituted system. We carefully designed an incubation—pull down—qPCR assay for this purpose (FIG. 8). After the HSV-1 C-capsid-nuclei incubation as previously described, the nuclei and extra-nuclear fluid were separated via low-speed centrifugation. The nuclei pellet sample was then re-suspended in surfactant (NP-40) containing buffer to break nuclear membrane. Nucleoplasm contents were thus released into the solution. A pull-down assay using anti-HSV1/2 ICP5/UL19 antibody and protein A beads were then performed to extract all the capsids away (along with those non-ejected, encapsidated viral DNAs). Any viral DNA traces left in the upper supernatant (sample-d) are from the intra-nuclear part. The pulled-down part (capsid pellets) was then treated with protease K to cut the protein-A beads off and digest the capsid shell, encapsidated viral DNA part (sample-d) was then extracted using phenol-chloroform method.

For the extra-nuclear fluid separated in the first centrifugation step, the same pull-down assay was performed to sediment all the non-nuclei associated capsids bound by HSV-1 antibody. This part of unbound capsids was quantified as sample-a. Any traces of free, non-encapsidated viral DNA in the extra-nuclear fluid is quantified as sample-b.

Figure 9:
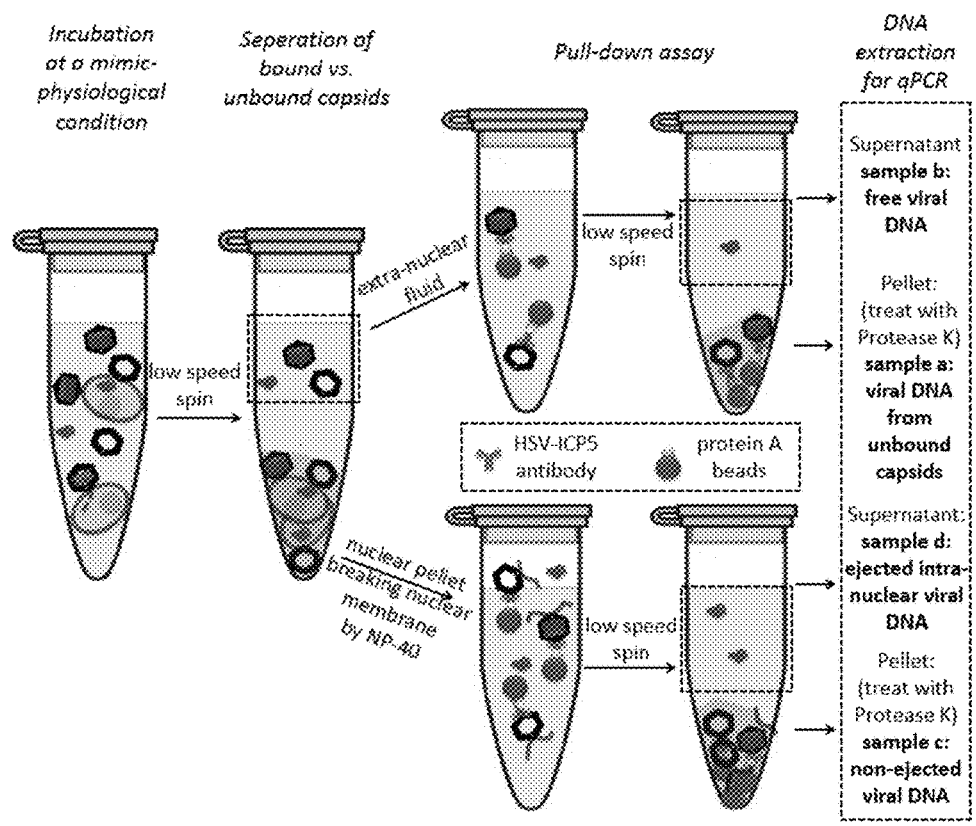
FIG. 9: Schematic of experimental assay to quantify DNA ejected from HSV-1 capsid into cell nuclei. HSV c-capsids were incubated with purified rat liver cell nuclei, in the presence or absence of osmolytes Dextran 155k and PEG 8k (osmolytes not shown in the cartoon). An assay was developed to separate and quantify each fraction of HSV-1 DNA from (a) extra-nuclear fluid (b) free capsids in the extra-nuclear fluid (c) nuclear content including chromosomal DNA and ejected viral DNA (d) capsids bound to the nuclear membrane. Note that HSV-1/2 ICP5 antibody has multiple binding sites on the capsids, only one is shown here for clarity. Host chromosomal DNA is in the sample (c) and not is shown in the cartoon. The final samples (a) to (d) collected were used to extract DNA by phenol-chloroform based purification method.

As a final step, we successfully isolated viral DNA samples by: (a) free, non-capsid associated viral DNA (known as the contamination part) in the extra-nuclear fluid; (b) viral DNA from unbound capsids; (c) viral DNA from nuclear-membrane associated, but non-ejected particles; (d) viral DNA successfully translocated into nucleoplasm. Following the experimental flow, after we effectively isolated viral DNA samples (a), (b), (c), (d) (FIG. 9 and FIG. 10A), we quantified HSV-1 gene copies in each sample using real-time qPCR analysis by custom TaqMan assays. Primers complimentary to VP16/UL48 and ICP0 sequences (located within IRL-IRS region) were chosen to estimate HSV-1 DNA copy numbers within our samples (Table in FIG. 5).

Figure 10:
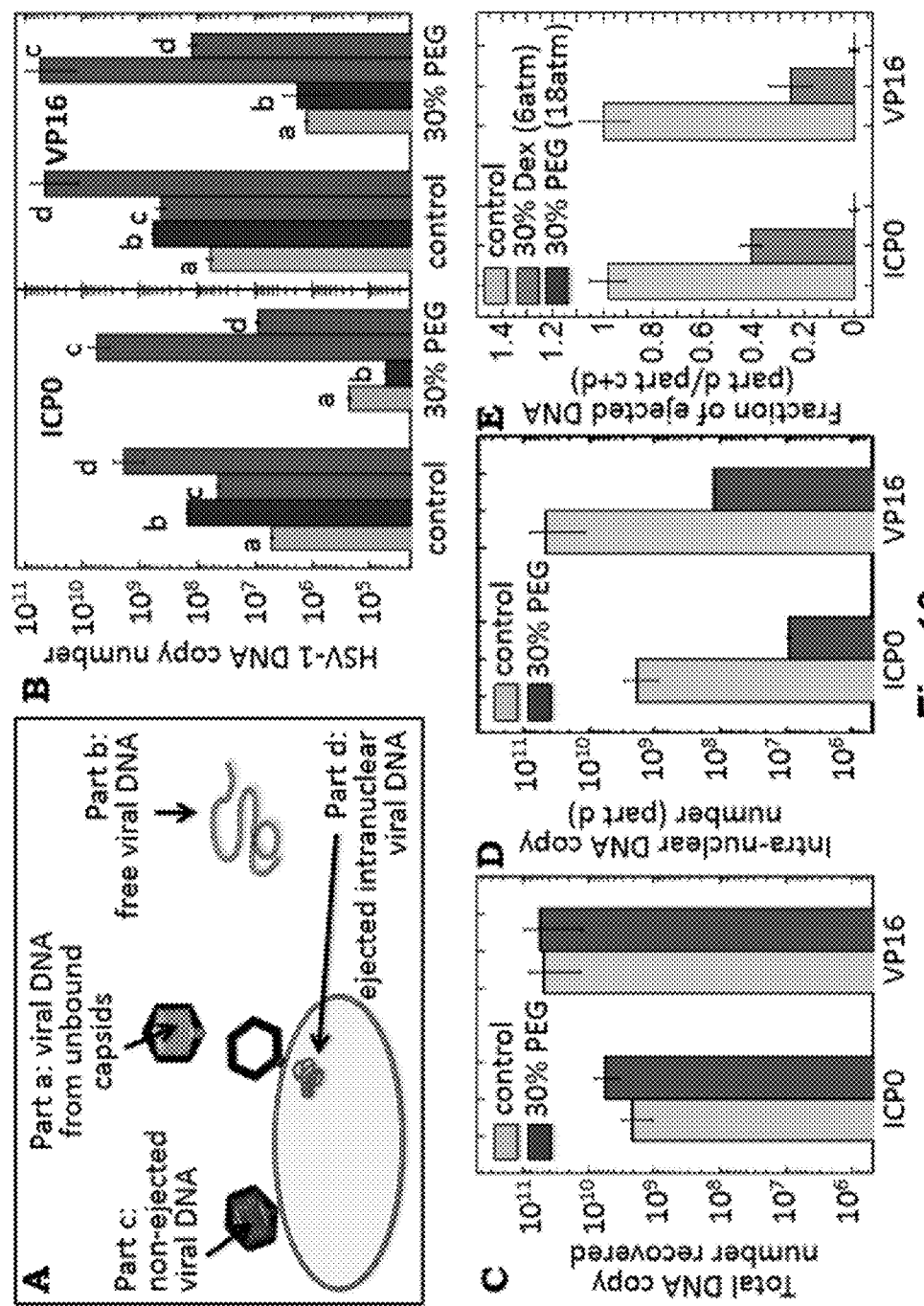
FIG. 10: Real time qPCR quantification of DNA fractions in our system. (A) Illustration of different DNA fractions in the system. (B) Absolute HSV DNA copy number calculated from each DNA sample from the assay described in FIG. 9. Copy numbers were quantified by real time qPCR method. DNA copy numbers were obtained based on standard curve set by serial diluted wild type HSV-1 DNA with known copy numbers. Primers based on ICP0 (upper panel) and VP16 (lower panel) sequences were both used for quantification of HSV genes. (C) Total amount of DNA recovered from this assay, in the presence and absence of osmolytes. Note that number in (C) is a sum of DNA quantities from a, b, c, d samples. (D) Intra-nuclear viral DNA copy number, corresponding to part d in Figure (B). (E) Ratio of intra-nuclear viral DNA copy number in "c" divided by total copy number of nuclei-associated viral DNA (c+d). "c/c+d" DNA ratio describes the efficiency of DNA ejection from nuclei-bound HSV-1.

When no osmolyte was introduced into the system, the majority of HSV-1 DNA isolated are intra-nuclear (sample-d in FIG. 10B) after 30 min incubation time at 37° C. and 95.5±4.4% of the total capsids have been nuclei-bound. Only a small fraction is from the capsids not associated with nuclei (0.1-0.2%, sample-a in FIG. 10B) or capsids in free form in extra-nuclear fluid (less than 7%, part b in FIG. 10B). By looking at percentage of intranuclear viral DNA copy number (sample-d) versus the total nuclei-associated viral copy number (sample-c+sample-d), we calculated that (98.4±0.9) % of those nuclei-associated viral particles released their DNA into the nuclei during the 30 min time frame (FIG. 10E). For any viral DNA that was not successfully ejected into the nuclei (ejected into extra-nuclear fluid instead), they will contribute to part b copy number instead.

As discussed earlier, sample-b consists of free, non-encapsidated DNA (including contaminant DNA) in the extra-nuclear fluid. However, for any capsids that fail to be pulled and precipitated out from the supernatant, their encapsidated DNA contributes to sample-b as well. This fraction of sample-b is DNase-protective as the protein shell is non-permeable to DNase. By adding DNase I to sample b, we can quantify this encapsidated DNA fraction, which relates to those unsuccessfully pulled capsids. Results show that this part only represented 1-6% of sample-b DNA.

Osmotic Suppression of HSV-1 DNA Ejection into the Nuclei.

Both ICP0 and VP16 qPCR results indicate that introduction of osmolytes did not interfere with our assay efficiency of DNA extraction. With presence or absence of 30% PEG, the total amount of DNA recovered from the assay (sum of DNA copy numbers from sample-a, b, c, d in FIG. 10B) approximately equals. This is important to show that quantity change of intra-nuclear DNA as we examined later (sample d) was not due to the change in total DNA extracted because of osmolytes. One thing to notice is that the DNA copy numbers in VP16 is in general one order of magnitude higher than that observed in ICP0 is due to the difference in qPCR efficiency because of primer-gene interactions.

With addition of 30% PEG-8k, the percentage of total nuclei-associated capsids. (sample-c+sample-d) slightly increased, from 95.5±4.4% to 99.9±0.0%. In parallel with the result that unbound en-capsidated and free viral DNA in extranuclear fluid (sample-a, b) decreased upon addition of PEG. This observation was likely due to the crowding effect of PEG, that osmolytes condense capsids around nuclei, thus enhancing the binding efficiency of capsids to nuclear membrane.

We can see that upon addition of 30% PEG-8k (18 atm), the nuclear membrane bound, non-ejected viral copy numbers (sample-c) dramatically increased in parallel with a significant drop of the intra-nuclear viral DNA (sample-d). The intra-nuclear viral DNA (sample-d) is of our most interests. Quantification of this sample gives us idea about viral translocation efficiency into the nucleoplasm. We can see in FIG. 4D, the amount of successfully ejected DNA into nucleoplasm dropped 99% with presence of PEG-8k. This striking decrease indicates a strong effect of osmolytes on DNA ejection. Earlier work done by the groups shows that PEG-8k at concentration of 30% w/w (corresponding to 18 atm, FIG. 10E) lead to complete suppression of genome release in a nuclear-free solution system by trypsin induced DNA ejection. This work confirms that in the reconstructed nuclei system where capsids are docked onto NPC, osmolytes again powerfully inhibits genome translocation into the nucleoplasm.

FIG. 10E shows the fraction of DNA ejected of the total nuclei-associated viral particles, sample-c/(sample-c+sample-d). We can see that with presence of 30% PEG, less than 0.3% percentage of DNA were ejected, which confirms a strong inhibition of DNA release due to osmotic pressure. To verify that this inhibition effect were non-osmolyte specific, we also repeated the experiment with presence of 30% dextran-155k, which can build an osmotic pressure of around 5.6 atm around in the extra-nuclear fluid. Viscosity of dextran 155k increased linearly with increasing concentration. For dextran 155k, 30% is the highest working concentration we can achieve. We can see that at this lower pressure, an average of 33% DNA were successfully ejected into the nucleoplasm. As shown later in the results, this correlates well with the in vitro, nuclei-free system of ejected DNA length portion at 5.6 atm (FIG. 11, discussed below).

HSV-1 DNA ejection lengths with increasing external osmotic pressure in a nuclei-free system.

To confirm the osmotic pressure effect on ejected DNA length in HSV-1 in our buffer system (with different ionic condition than previously published), we repeated the experiments using pulse-field electrophoresis (PFGE) to measure the (non-) ejected length of DNA fragments with increasing PEG 8000 concentration. Similar experiments were also done with Dextran-155k. In this assay, the DNA ejection from HSV-1 was triggered with trypsin, followed with DNase I treatment, and the non-ejected DNA within capsids was then extracted by SDS and protease K treatment and loaded onto PFGE for gel analysis. As shown in FIG. 11, one can see that the presence of 25% PEG w/w would completely suppressed DNA ejection, which corresponds to an internal pressure of ~11 atm within HSV-1 capsids balanced by an external osmotic pressure of equal magnitude.

Previous results show that encapsidated viral DNA pressure is dependent on cation ionic strength of the sitting buffer. HSV-1 genome pressure was measured to be 18 atm in TM buffer (50 mM Tris, 10 mM $MgSO_4$, pH7.4) with ionic strength of 0.02 M. In this assay, the ionic strength of CBB buffer is 0.054 M, about 2.5 fold of that in TM buffer. Additional cations in solution help in screening viral DNA surface charge, thus reducing inter-strand repulsions and lowered the encapsidated DNA pressure. Dextran-155k were shown to have similar inhibition effect at concentrations up to 30% (which corresponds to 5.6 atm). The fact that in our isolated-nuclei assay, a mean of 33% DNA were ejected with 30% Dextran (average value from ICP0 and VP16 result) and 0.2% DNA were ejected with 30% PEG correspond well with these nuclei-free assay result.

The following clauses provide examples of various aspects of the invention described herein.

1. A method of treating an infection in a patient of a virus having a stressed nucleic acid genome in a capsid, comprising contacting a virus particle of the virus with an amount of a composition comprising a polycationic polypeptide, a polycationic polymer, a DNA condensing protein, a cationic dendrimer, a branched polyamine, an inorganic cationic metal complex, a cationic surfactant, an osmolyte, and/or a chelating agent in an amount effective to inhibit release of the nucleic acid from the capsid of the virus particle and/or to interfere with packaging of viral genomes, thereby treating the virus infection.

2. The method of clause 1, wherein the virus particle is contacted with an amount of a chelating agent effective to inhibit release of nucleic acid from the capsid of the virus particle.

3. The method of clause 2, wherein the chelating agent is selected from the group consisting of: EDTA (ethylene diamine tetra-acetic acid), EGTA (ethylene glycol tetraacetic acid), an aminopolycarboxylic acid, DMPS (2,3-dimercapto-1-propanesulfonic acid), DMSA (dimercaptosuccinic acid or succimer) an antibiotic drugs of the tetracycline and quinolone families, citric acid, phosphonates, and enterobactin.

4. The method of clause 1, wherein the virus particle is contacted with an amount of an osmolyte, effective to inhibit release of nucleic acid from the capsid of the virus particle.

5. The method of clause 4, wherein the osmolyte is a PEG or a dextran.

6. The method of clause 1, wherein the virus particle is contacted with an amount of a polycationic polypeptide effective to inhibit release of nucleic acid from the capsid of the virus particle.

7. The method of clause 6, wherein the polycationic polypeptide is selected from the group consisting of: poly-L-arginine, poly-L-lysine, polyornithine, and copolymers comprising two or more arginine, lysine, or ornithine residues.

8. The method of clause 1, wherein the virus particle is contacted with an amount of a cationic dendrimer, a polycationic polymer, an inorganic cationic metal complex, and/or a cationic surfactant effective to inhibit release of nucleic acid from the capsid of the virus particle.
9. The method of clause 8, wherein the cationic dendrimer, the polycationic polymer, the inorganic cationic metal complex, and/or the cationic surfactant is a poly(amidoamine) (PAMAM) dendrimer, G0-PAMAM (+4), G1-PAMAM (+8), hexaamminecobalt(III) chloride, branched polyethylenimine, CTAB, DTAB, TTAB, and/or a pharmaceutically acceptable salts thereof.
10. The method of clause 1, wherein the virus particle is contacted with an amount of a DNA condensing protein effective to inhibit release of nucleic acid from the capsid of the virus particle.
11. The method of clause 10, wherein the DNA condensing protein is histone H1, histone H2A, histone H2B, histone H3, histone H4, transition nuclear protein 1, or transition nuclear protein 2.
12. The method of clause 1, wherein the virus particle is contacted with an amount of a polycationic composition effective to inhibit release of nucleic acid from the capsid of the virus particle.
13. The method of clause 12, wherein the polycationic composition comprises salmon protamine, $Mn^{2+}$; a biogenic amine, dimethylamine $((CH_2)_3NH)^+$, putrescine $(NH_2(CH_2)_4NH_2)^{2+}$, spermidine $(H_2N(CH_2)_3NH(CH_2)_4NH_2)^{3+}$, spermine $(H_2N(CH_2)_3NH(CH_2)_4—NH(CH_2)_3NH_2)^{4+}$, and/or a pharmaceutically acceptable salt of any of the preceding.
14. The method of any one of clauses 1-13, wherein the virus is an adenovirus, a reovirus, or a lentivirus.
15. The method of any one of clauses 1-13, wherein the virus is a herpesvirus.
16. The method of clause 14, wherein the virus is a Herpes simplex virus 1 (HSV-1), Herpes simplex virus 2 (HSV-2), Human cytomegalovirus (CMV), Varicella Zoster virus (VZV), Epstein Barr virus (EBV), Human herpes virus 6 (HHV-6), Human herpes virus 7 (HHV-7), or Human herpes virus 8 (HHV-8).
17. The method of any one of clauses 1-16, wherein the virus is a herpes simplex virus.
18. The method of clause 1, wherein the composition is administered topically to a patient.
19. The method of clause 18, wherein the virus is HSV or VZV, and the composition is administered topically to a herpes simplex, chickenpox, or shingles lesion.
20. The method of clause 18, wherein the virus is CMV and the composition is administered to the eye or ear of the patient, and optionally prophylactically.
21. A method of treating shingles in a patient, comprising topically administering a composition according to any one of clauses 1-13 to a shingles lesion of a patient having shingles, in an amount effective to treat shingles in a patient.
22. A method of treating herpes simplex virus in a patient, comprising topically administering a composition according to any one of clauses 1-13 to a herpes simplex virus lesion of a patient, in an amount effective to treat a herpes simplex virus lesion in a patient.
23. A method of treating chickenpox in a patient, comprising topically administering a composition according to any one of clauses 1-13 to a chickenpox lesion of a patient, in an amount effective to treat chickenpox in a patient.
24. A method according to any one of clauses 17-22, further comprising administering concurrently to the patient an antiviral drug other than the polycationic polypeptide, the polycationic polymer, the DNA condensing protein, the cationic dendrimer, the branched polyamine, the osmolyte, the inorganic cationic metal complex, the cationic surfactant, and/or the chelating agent to the patient.

This invention was also supported by: Swedish Research Council (Vetenskapsrådet) Grant No. 622-2008-726 (to AE)

Having described this invention, it will be understood to those of ordinary skill in the art that the same can be performed within a wide and equivalent range of conditions, formulations and other parameters without affecting the scope of the invention or any embodiment thereof.

I claim:

1. A method of treating an infection in a patient of a herpesvirus having a stressed nucleic acid genome in a capsid, comprising administering to the patient a composition comprising a branched polyethylenimine able to permeate the capsid of the virus in an amount effective to inhibit release of the nucleic acid from the capsid of the herpesvirus and/or to interfere with packaging of herpesvirus viral genomes, and a pharmaceutically acceptable excipient, thereby treating the herpesvirus infection.

2. The method of claim 1, wherein the branched polyethylenimine is able to permeate the capsid of the virus to inhibit release of nucleic acid from the capsid of the virus particle.

3. The method of claim 1, wherein the herpesvirus is a Herpes simplex virus 1 (HSV-1), Herpes simplex virus 2 (HSV-2), Human cytomegalovirus (CMV), Varicella Zoster virus (VZV), Epstein Barr virus (EBV), Human herpes virus 6 (HHV-6), Human herpes virus 7 (HHV-7), or Human herpes virus 8 (HHV-8).

4. The method of claim 1, wherein the composition is administered topically to the patient.

5. The method of claim 4, wherein the herpesvirus is Herpes simplex virus (HSV) or Varicella Zoster virus (VZV), and the composition is administered topically to a herpes simplex, chickenpox, or shingles lesion.

6. The method of claim 4, wherein the herpesvirus is CMV and the composition is administered to the eye or ear of the patient.

7. The method of claim 1, further comprising administering concurrently to the patient an antiviral drug other than the branched polyethylenimine.

8. The method of claim 1, wherein the branched polyethylenimine has a size ranging from 360 Da to 1,268 kDa.

* * * * *

SEQUENCE LISTING

```
<160> NUMBER OF SEQ ID NOS: 7

<210> SEQ ID NO 1
<211> LENGTH: 20
<212> TYPE: DNA
<213> ORGANISM: Epstein-Barr Virus (Human herpesvirus 4)

<400> SEQUENCE: 1
cccaggagtc ccagtagtca                                              20

<210> SEQ ID NO 2
<211> LENGTH: 20
<212> TYPE: DNA
<213> ORGANISM: Epstein-Barr Virus (Human herpesvirus 4)

<400> SEQUENCE: 2
cagttcctcg ccttaggttg                                              20

<210> SEQ ID NO 3
<211> LENGTH: 20
<212> TYPE: DNA
<213> ORGANISM: Human herpesvirus 6
```

```
<400> SEQUENCE: 3
ccttgatcat tcgaccgttt                                                    20

<210> SEQ ID NO 4
<211> LENGTH: 20
<212> TYPE: DNA
<213> ORGANISM: Human herpesvirus 6

<400> SEQUENCE: 4
tgggattggg attagagctg                                                    20

<210> SEQ ID NO 5
<211> LENGTH: 23
<212> TYPE: DNA
<213> ORGANISM: Human herpesvirus-8 (Kaposi's sarcoma-associated
      herpesvirus)

<400> SEQUENCE: 5
ttccccagat acacgacaga atc                                                23

<210> SEQ ID NO 6
<211> LENGTH: 17
<212> TYPE: DNA
<213> ORGANISM: Human herpesvirus-8 (Kaposi's sarcoma-associated
      herpesvirus)

<400> SEQUENCE: 6
cggagcgcag gctacct                                                       17

<210> SEQ ID NO 7
<211> LENGTH: 17
<212> TYPE: DNA
<213> ORGANISM: Human herpesvirus-8 (Kaposi's sarcoma-associated
      herpesvirus)

<400> SEQUENCE: 7
cctacgtgtt cgtcgac                                                       17
```